United States Patent
Abe et al.

(10) Patent No.: US 6,638,221 B2
(45) Date of Patent: Oct. 28, 2003

(54) ULTRASOUND DIAGNOSTIC APPARATUS, AND IMAGE PROCESSING METHOD

(75) Inventors: Yasuhiko Abe, Otawara (JP); Ryoichi Kanda, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/247,559

(22) Filed: Sep. 20, 2002

(65) Prior Publication Data

US 2003/0083578 A1 May 1, 2003

(30) Foreign Application Priority Data

Sep. 21, 2001 (JP) .................................. 2001-288499

(51) Int. Cl.$^7$ .................................................. A61B 8/00
(52) U.S. Cl. ........................ 600/437; 600/453; 600/456; 600/438
(58) Field of Search ................... 600/437–472

(56) References Cited

U.S. PATENT DOCUMENTS

| | | | | |
|---|---|---|---|---|
| 5,441,052 A | * | 8/1995 | Miyajima | 600/455 |
| 5,544,656 A | * | 8/1996 | Pitsillides et al. | 600/450 |
| 5,622,174 A | * | 4/1997 | Yamazaki | 600/441 |
| 5,785,654 A | * | 7/1998 | Iinuma et al. | 600/441 |
| 5,840,028 A | * | 11/1998 | Chubachi et al. | 600/437 |
| 6,099,471 A | * | 8/2000 | Torp et al. | 600/438 |
| 6,106,465 A | * | 8/2000 | Napolitano et al. | 600/443 |
| 6,352,507 B1 | * | 3/2002 | Torp et al. | 600/438 |

FOREIGN PATENT DOCUMENTS

| | | |
|---|---|---|
| JP | 9-201361 | 8/1997 |
| JP | 11-155862 | 6/1999 |
| JP | 2001-70303 | 3/2001 |

* cited by examiner

*Primary Examiner*—Marvin M. Lateef
*Assistant Examiner*—William C. Jung
(74) *Attorney, Agent, or Firm*—Oblon, Spivak, McClelland, Maier & Neustadt, P.C.

(57) ABSTRACT

Two-dimensional distribution data of velocities on a moving object in an object to be examined is obtained. A motion field which defines the motion direction of a tissue is stored. A plurality of tracking points are obtained in a tissue range in the two-dimensional distribution data. The moving positions of the tracking points are estimated and the positions are sequentially tracked. Velocities toward the motion direction defined by the motion field are obtained on the basis of the two-dimensional distribution data. One intermediate output value is obtained by performing a predetermined computation by using velocities toward the motion direction at tracking positions of at least two tracking points in each time phase. The values of intermediate positions are obtained by performing weighted addition of intermediate outputs at different positions. A display image is generated and displayed by using the values of the intermediate positions.

30 Claims, 16 Drawing Sheets

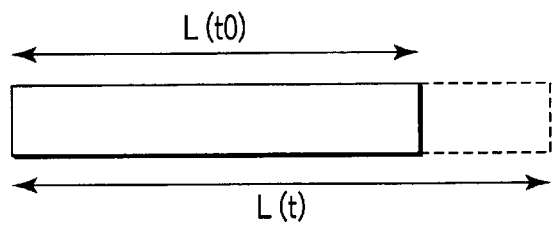
FIG. 1B
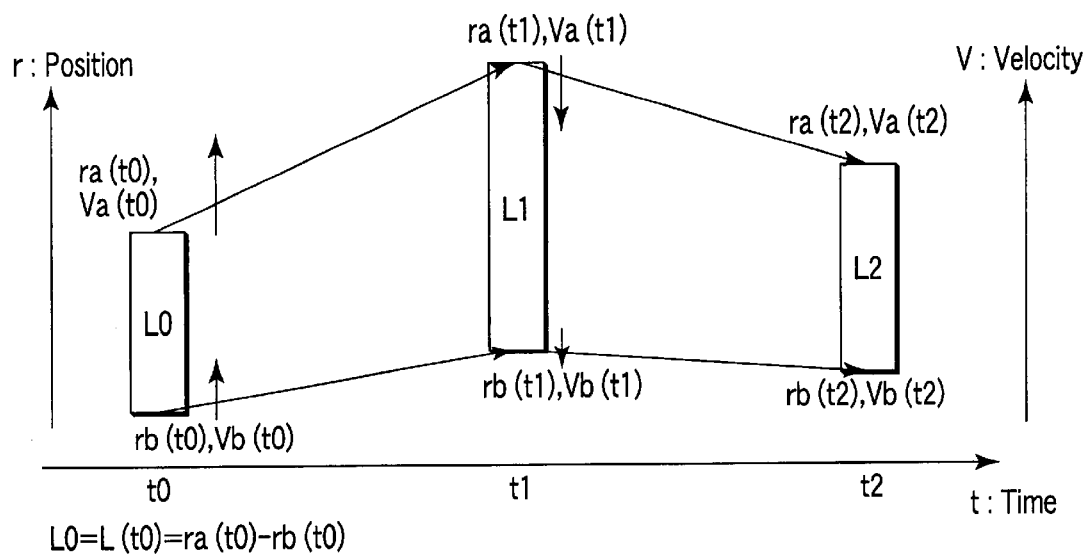
$L0 = L(t0) = ra(t0) - rb(t0)$
FIG. 2
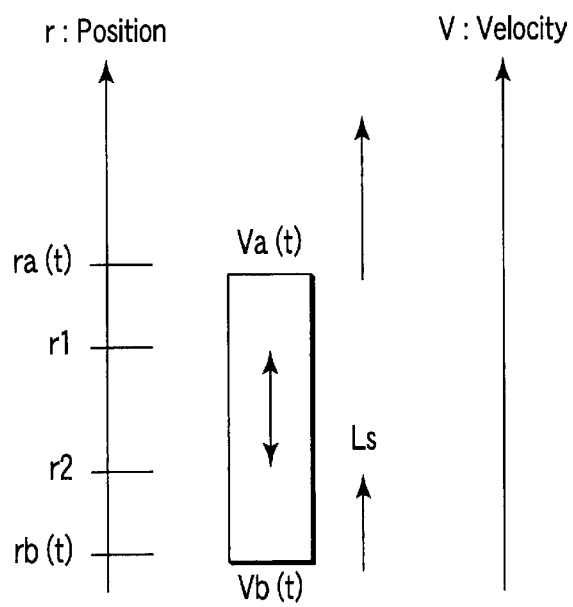
FIG. 3    $L(t) = ra(t) - rb(t)$

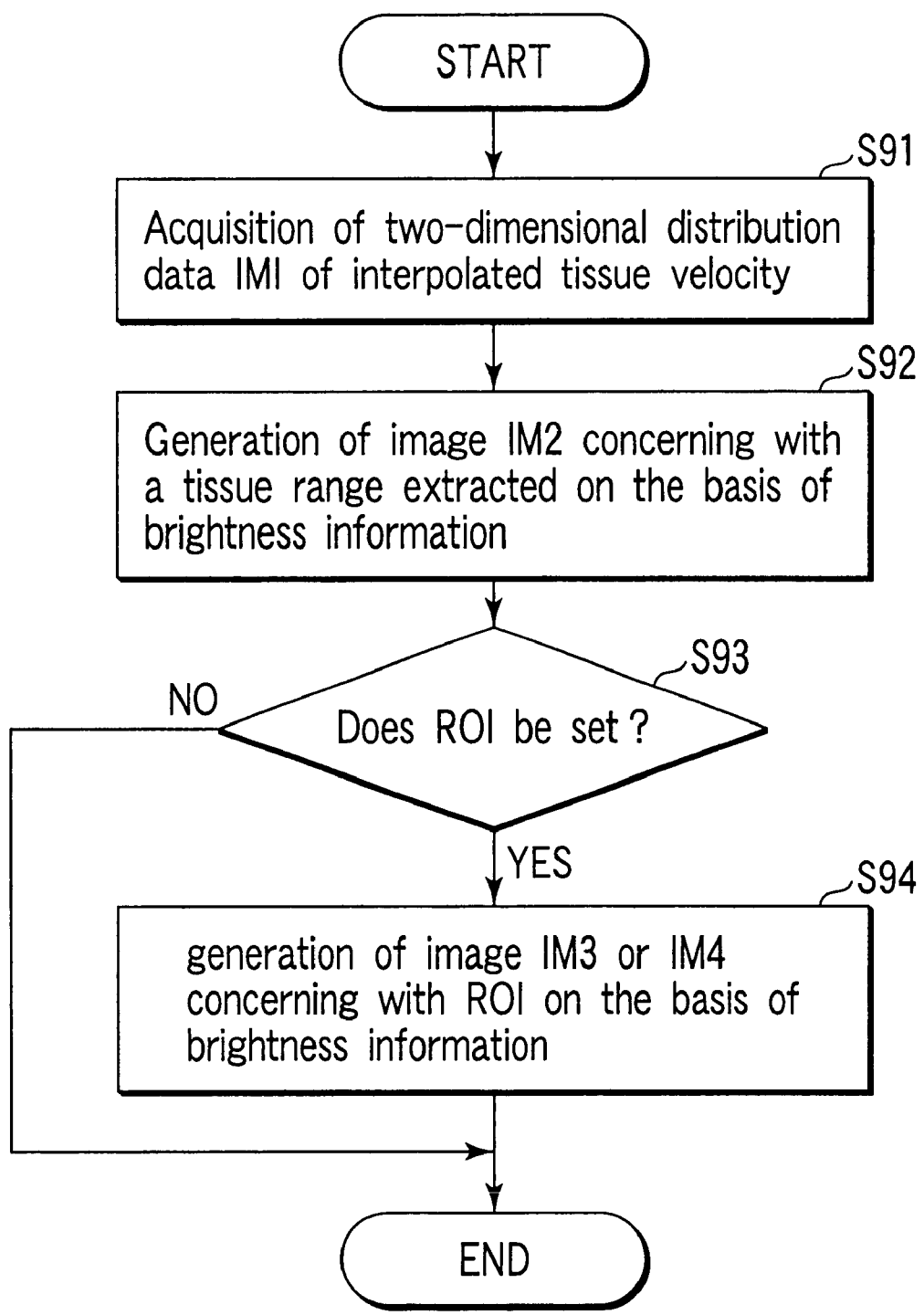
F I G. 9A

Four- and two-chamber images from apex of heart

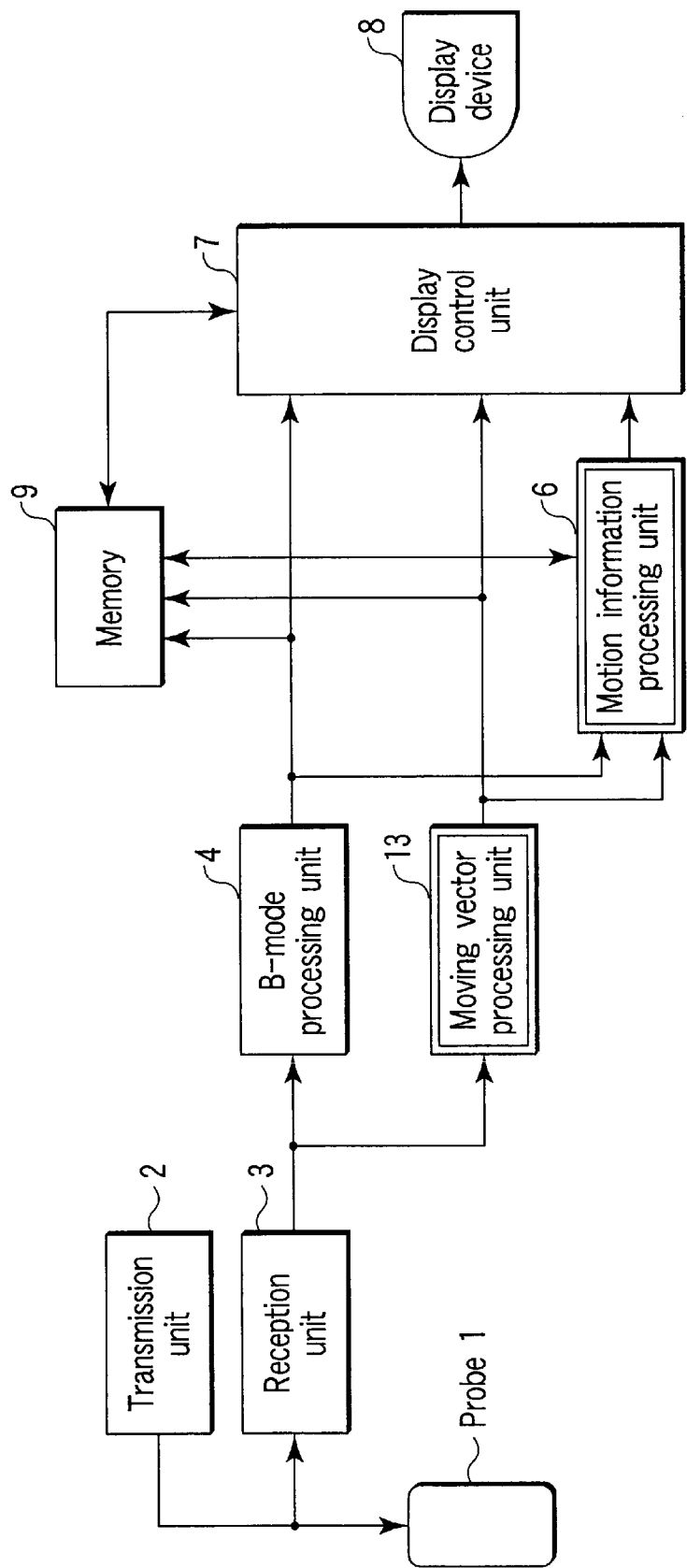
F I G. 14A

ULTRASOUND DIAGNOSTIC APPARATUS, AND IMAGE PROCESSING METHOD

CROSS-REFERENCE TO RELATED APPLICATIONS

This application is based upon and claims the benefit of priority from the prior Japanese Patent Applications No. 2001-288499, filed Sep. 21, 2001; and No. 2002-272845, filed Sep. 19, 2002, the entire contents of both of which are incorporated herein by reference.

BACKGROUND OF THE INVENTION

1. Field of the Invention

The present invention relates to an ultrasound diagnostic apparatus, image processing apparatus, motion information image generating method which provide effective information for medical diagnoses.

2. Description of the Related Art

It is very important for the diagnosis of living tissue such as the myocardium to objectively and quantitatively evaluate the function of the tissue. For example, conventional quantitative evaluation methods mainly associated with the heart will be described below.

A method using the myocardial velocity gradients (MVG) defined by two-dimensional images is disclosed in Jpn. Pat. Appln. KOKAI Publication No. 11-155862. The MVGs defined by two-dimensional images include an MVG-S for a short-axis plane and an MVG-L for a long-axis plane (four- or two-chamber plane based on an apical long-axis). According to currently practical MVG-S/L, a region of the myocardium and its local motion direction can be determined by manually setting the contours of the endocardium and epicardium coats of the myocardium in a two-dimensional image at a given time phase, and a myocardial velocity gradient, i.e., a strain rate, is obtained in each range of the myocardium.

Jpn. Pat. Appln. KOKAI Publication No. 9-201361 discloses an MVG-M method in which when the positions of two points (preferably on the endocardium and epicardium coats) of the myocardium are given at an initial time phase, the positions of two points (on the endocardium and epicardium coats) are automatically tracked at other time phases by using the TDT (Tissue Doppler Tracking) method, thereby obtaining MVGs at all the time phases. A technique of obtaining a strain as a value representing tissue deformation and displaying it in real time is also disclosed in Jpn. Pat. Appln. KOKAI Publication No. 2001-70303.

The significance of obtaining motion parameters in a local range inside the myocardium is described in reference 1 ("Difference between Endocardial Myocardium and Epicardial Myocardium of Left Ventricular Wall", J Cardiol 2000; 35: 205–218). According to this reference, in the case of the healthy myocardium, the endocardium coat side contributes to contraction more dominantly (about twice) than the epicardium coat side, whereas in a case of ailment, e.g., cardiac infarction, this contribution of the endocardium coat side reduces. Although this fact has been known from animal experiments, recent studies using the MVG-M to be described later and the like have revealed that the same applies to humans. The noninvasive, quantitative evaluation of local functions inside the myocardium as well as the function of the overall myocardium is expected to be useful for the comprehension of the progress of a disease and the selection of a medical treatment for the disease, and hence has gained in importance.

In the conventional MVG method, however, in order to analyze a plurality of time phases of the cardiac time phases, a myocardial region must be set in each of the time phases, resulting in difficulty in analyzing changes in MVG-S/L over time. In addition, since MVG-S/L is used to obtain a motion parameter based on the size of the myocardium, such as the demarcation size of the myocardium, it is difficult to obtain distribution information in a local range inside the myocardium.

In the conventional MVG-M method, since the velocity gradient of an M-mode image is displayed, temporal analysis can be performed relatively easily. However, in the MVG-M method, since only one-dimensional information is provided, two-dimensional distribution information cannot be obtained.

In addition, a characteristic common to computations of strain rates such as velocity gradients is that spatial differentiation is performed by using velocity information that tends to be spatially unstable due to the influence of speckle noise and the like unique to ultrasounds. For this reason, it is difficult to perform stable computations concerning a living body due to noise.

In the conventional strain display method, the strain rate between two points of a region having a fixed length temporally is obtained on the assumptions that the region has spatially uniform strain, and the strain is included in a predetermined interval. These assumptions do not hold in the case of evaluation of the heart, especially a short-axis plane. Therefore, accurate strain cannot be obtained.

BRIEF SUMMARY OF THE INVENTION

The present invention has been made in consideration of the above situation, and has as its object to provide an ultrasound image apparatus, and motion information image generating method which provide a motion information image representing displacement or strain with high stability even if the image is generated from a living tissue such as the heart.

In order to achieve the above object, the present invention has the following means.

The present invention may provide an ultrasonic diagnostic apparatus which comprises: a memory which stores a plurality of ultrasonic images which corresponds to a plurality of time phases and are concerning with an object; a distribution image generation unit configured to generate a plurality of distribution images of motion velocities in the plurality of the time phases on the basis of the plurality of the ultrasonic images; a tracking point setting unit configured to set tracking points in a tissue range of the object in an image which is one of the plurality of ultrasonic images and corresponds to a predetermined time phase; an estimation unit configured to estimate corresponding points which correspond to the tracking points in the plurality of ultrasound images corresponding to remaining time phases other than the predetermined time phase, on the basis of the plurality of distribution images of motion velocities; a signal value determining unit configured to determine signal values at the tracking points and the corresponding points in each of the plurality of the time phases according to stretch of the tissue range of the object; a motion information image generating unit configured to generate a motion information image on the basis of the signal values at the tracking points and the corresponding points; and a display unit configured to display the motion information image.

The present invention may provide an ultrasonic diagnostic apparatus which comprises: a memory which stores a plurality of ultrasonic images which corresponds to a plurality of time phases and are concerning with an object; a center point of contraction setting unit configured to set a first center point of contraction in a tissue range of the object and a second center point of contraction adjacent to the first center point of contraction; a distribution image generation unit configured to generate a first distribution images of motion velocities in a direction toward the first center point of contraction and a second distribution images of motion velocities in a direction toward the second center point of contraction on the basis of the plurality of the ultrasonic images; a tracking point setting unit configured to set tracking points in a tissue range of the object in an image which is one of the plurality of ultrasonic images and corresponds to a predetermined time phase; an estimation unit configured to estimate first corresponding points which correspond to the tracking points on the basis of the first distribution images of motion velocities and second corresponding points which correspond to the tracking points on the basis of the second distribution images of motion velocities, in the plurality of ultrasound images corresponding to remaining time phases other than the predetermined time phase; a signal value determining unit configured to determine signal values at the tracking points associated with a stretch of the tissue range in each of the time phases and signal values at the first corresponding points and the second corresponding points in the remaining time phases other than the predetermined time phase; a motion information image generating unit configured to generate a first motion information image on the basis of the signal values at the tracking points and the first corresponding points and a second motion information image on the basis of the signal values at the tracking points and the second corresponding points; a compound image generating unit configured to generate a compound image compounded the first motion information image and the second motion information image; and a display unit configured to display the compound image.

The present invention may provide a motion information image generating method which comprises: generating a plurality of distribution images of motion velocities in a plurality of time phases on the basis of a plurality of a ultrasonic images which corresponds to a plurality of time phases and are concerning with an object; setting tracking points in a tissue range of the object in an image which is one of the plurality of ultrasonic images and corresponds to a predetermined time phase; estimating corresponding points which correspond to the tracking points in the plurality of ultrasound images corresponding to remaining time phases other than the predetermined time phase, on the basis of the plurality of distribution images of motion velocities; determining signal values at the tracking points and the corresponding points in each of the plurality of the time phases according to stretch of the tissue range of the object; generating a motion information image on the basis of the signal values at the tracking points and the corresponding points; and displaying the motion information image.

BRIEF DESCRIPTION OF THE SEVERAL VIEWS OF THE DRAWING

FIG. 1B is a conceptual view for explaining the definition of strain;

FIG. 2 is a conceptual view for explaining Lagrangian strain;

FIG. 3 is a conceptual view for explaining natural strain;

FIG. 9A is a flowchart showing a flow of the groups of the tracking points setting processing;

FIG. 14A is a block diagram showing the schematic arrangement of an ultrasound diagnostic apparatus according to the second embodiment;

DETAILED DESCRIPTION OF THE INVENTION

Figure 1A:
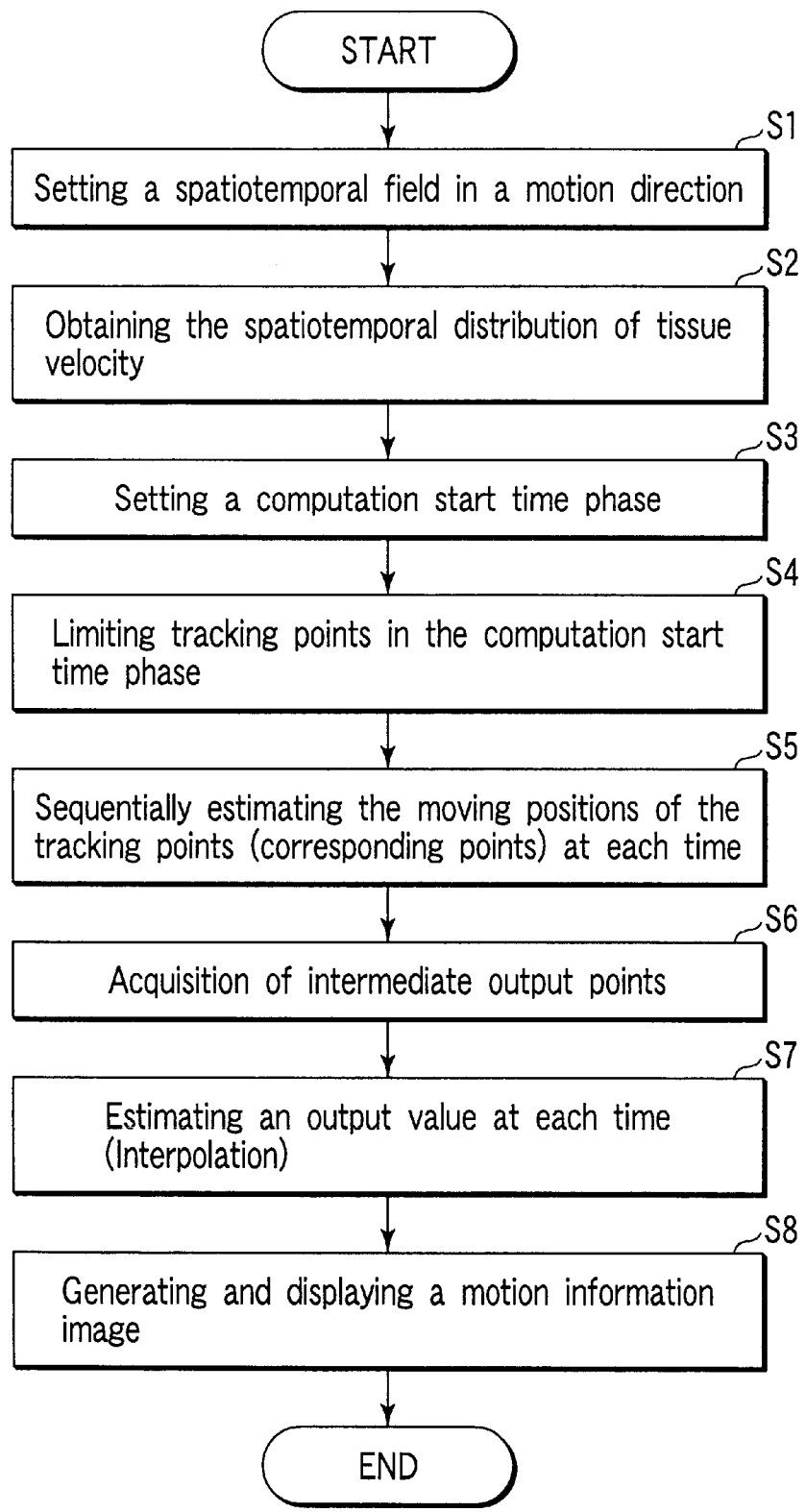
FIG. 1A is a flowchart showing a flow of motion information image acquisition processing executed by the ultrasonic diagnostic apparatus according to the first embodiment.

The first and second embodiments of the present invention will be described below with reference to the views of the accompanying drawing. The same reference numerals denote constituent elements having substantially the same functions and arrangements in the following description, and a repetitive description will be made only when required.

(First Embodiment)

In the first embodiment, motion information in which noise is reduced by time integration is computed on the basis of the velocity information of a tissue, and the resultant spatial distribution is provided as an image. The obtained motion information image is the image information of displacement or strain with respect to a predetermined motion direction.

In this case, in order to effectively obtain a high-quality motion information image of a tissue with motion, it is important to process velocity information obtained from the tissue while tracking the position of the tissue. In the case of myocardium, in particular, since the movement amount is large, position tracking is indispensable for preventing a target treatment position from falling outside a myocardium region (e.g., a heat chamber). Position tracking is also an important factor for the acquisition of a local motion information distribution inside the myocardium.

In order to actually obtain a motion information image accompanying such local tissue position tracking (to be referred to as tissue tracking imaging hereinafter), the following means are used:

[1] (Step S1) setting a spatiotemporal field in a motion direction (Motion-Field: MF);

[2] (Step S2) obtaining the spatiotemporal distribution of tissue velocity (Velocity-Field: VF);

[3] (Step S3) setting a computation start time phase;

[4] (Step S4) limiting an area (tracking points) of the tissue to be tracked in the computation start time phase;

[5] (Step S5) sequentially estimating the moving positions of the tracking points at each time by using VF•(using also MF in the tissue Doppler method) time intervals;

[6] (Step S6) defining an input signal by using MF at each point of the tracking points and performing integration up to each time (acquisition of intermediate output points); and

[7] (Step S7) estimating an output value at each time and each point of an output image by using the value of the nearest intermediate outputs.

[8] (Step S8) generating and displaying a motion information image

In the case where an acquisition of a displacement image is executed, a displacement is defined by using a velocity as an input signal in the process [6].

In the case where an acquisition of a strain image is executed, an ideal strain definition will be provided by using the two types of definitions described below (Lagrangian strain, Natural strain). These definitions are obtained by a technique of temporally tracking the positions of a pair of points, i.e., one point determined by an initial time phase with respect to a one-dimensional rod-like tissue model and the other point having a predetermined initial length from this point. Note that such strain is described in reference 2 ("Regional Strain and Strain Rate Measurements by Cardiac Ultrasound: Principles, Implementation and Limitations", Eur J Echocardiography (2000) 1, 154-70).

[Lagrangian Strain]

Lagrangian strain is a unit strain defined by equation (1) with reference to an initial length L(t0). Note that FIG. 1 shows the relationship between L(t0) and L(t).

$$S_L(t) = [L(t) - L(t0)]/L(t0) \quad (1)$$

where $S_L(t)$ is the Lagrangian strain, and L(t0) is the length at reference time t0.

In addition, Lagrangian strain can be calculated by obtaining displacements from integration of the velocities at the respective points of the pair of points tracked and normalizing the difference between the pair of displacements with the initial length. A specific procedure for this operation will be described below. FIG. 2 is a conceptual view of the procedure.

(1) Two points (points a and b) having a distance L0 are set at time phase t0. Note that ra(t0) and rb(t0) represent the positions of the points a and b at t0, respectively.

(2) L(t)=ra(t)−rb(t) is calculated while the positions of these two points are temporally tracked.

(3) $S_L(t)$=(L(t)−L0)/L0 is calculated, where L(t) is represented by equation (2) given below and $S_L(t)$ can be obtained by equation (3-1) or (3-2).

$$L(t) = \int Va(\tau)d\tau - \int Vb(\tau)d\tau + L0 \quad (2)$$

$$S_L(t) = (\text{tracking displacement of the point } a - \text{tracking displacement of the point } b)/L0 \quad (3\text{-}1)$$

$$= \int [(\text{tracking displacement of the point } a - \text{tracking displacement of the point } b)/L0]d\tau \quad (3\text{-}2)$$

Assume that the integration interval is (t0≦τ≦t). In addition, Va(τ) and Vb(τ) represent the tracking velocities at the points a and b.

The numerator of the integrand of equation (3-2) is corresponding to definition of an ideal strain rate. If defines this strain rate is output without integration, an ideal strain rate obtained by tissue tracking can be obtained as an output image. Note, however, that a strain rate image itself is susceptible to the influence of noise. In this embodiment, therefore, in consideration of strain, letting $S_N(t)$ be natural strain and L(t) be the length at time t, these values are formulated like:

$$S_N(t) = \int [(La(x+\tau) - L(x))/L(x)]dx \quad (4)$$

Note that $SR_N(\tau) = (La(\tau+\Delta t) - L(\tau))/L(\tau)$, and the integration interval is (t0≦τ≦t), letting Δ means differential period.

In addition, $S_L(t)$ and $S_N(t)$ can be related to each other by:

$$S_N(t) = \ln(1 + S_L(t)) \text{ or } S_L(t) \exp[S_N(t)] - 1 \quad (5)$$

As indicated by equation (4), natural strain can be calculated by calculating the difference of the velocities between a pair of points separated from each other by predetermined length under a predetermined condition, obtaining a strain rate $SR_N(\tau)$ by normalizing the difference between the two points, and integrating the strain rate. A specific condition for this operation will be described below. FIG. 3 is a conceptual view of this procedure.

As shown in FIG. 3, two points (points a and b) having the length L(t) is set at time phase t. In this case, ra(t) and rb(t) represent the positions of the points a and b at time phase t. Assuming that the strain within L(t) is uniformly linear, two points (r1 and r2) having a fixed length Ls are set within the length L(t). In such setting, the strain rate (velocity gradient) between r1 to r2 is equal to natural strain rate (SRN(t)). Note that SRN(t) is expressed by:

$$\begin{aligned}VG(t) &= (V(r1, t) - V(r2, t))/(r1 - r2) \\ &= [Vb(t) + (Va(t) - Vb(t))/L(t) * (r1 - rb(t))] - \\ &\quad [Vb(t) + (Va(t) - Vb(t))/L(t) * (r2 - rb(t))]/(r1 - r2) \\ &= (Va(t) - Vb(t))/L(t) * (r1 \cdot r2)/(r1 \cdot r2) \\ &= (Va(t) - Vb(t))/L(t) \\ &= SRN(t)\end{aligned} \quad (6)$$

wherein, V(r,t)=Vb(t)+(Va(t)−Vb(t))/L(t)*(r(t)−rb(t))

By using equation (6), $S_N(t)$ can be calculated by time integration from t0 to t with respect to the velocity gradient (VG(τ)) between r1 to r2, and $S_L(t)$ is calculated by the transformation $S_L(t) = \exp(S_N(t)) - 1$. In the present embodiment, a example of using Lagrangian strain will be described hereinafter.

As a conventional technique associated with such tissue tracking imaging, Jpn. Pat. Appln. KOKAI Publication No. 2001-70303 discloses a method of calculating and displaying tissue deformation in real time. This method and the method in the present invention, however, differ in their specific methods of defining a strain. In the conventional technique, as shown in FIG. 3, a strain is estimated with reference to an instantaneous length by using an assumption, and an ideal strain is obtained by transformation. Therefore, in order to make this result match with the ideal strain definition, the following limitation caused by obtaining the strain rate between two points having a temporally fixed length. That is, since only one point is tracked in the conventional technique, the assumption that the two points are included in an interval in which a spatially uniform strain exists does not hold for the evaluation of the heart concerned with a short-axis plane especially.

In general, an ultrasound signal is affected by speckle noise and the like. In order to obtain a spatially stable strain rate, this fixed length must be kept long to a certain extent (in practice, about 4 to 10 mm because it is said that the autocorrelation length of speckle is on the order of several mm). Therefore, the scheme of the present embodiment, in which two points are directly tracked, is effective in including these two points in a myocardium region that moves. According to the prior art, attempts have been made to improve the precision of a strain rate by calculating the weighted mean of strain rates obtained with several different fixed lengths and spatially and adaptively changing the fixed length (not by tracking two points temporally). In either of these methods, however, two points are not directly tracked, and only a limited improving effect can be actually obtained because of limitations such as the above speckle.

Although the arrangements of [4] and [7] are necessary when high-quality tissue tracking imaging is to be actually realized.

More specifically, [4] is designed to limit a tissue range. An initial tracking point is set in the tissue but is not set in the heart chamber. If such a range other than the tissue is excluded in advance from tracking points, the value of a region other than the tissue is added to an output image at the time of interpolation of the output image. It is therefore preferable to limit a tissue range.

In addition, [7] is an effective method for estimating a uniform output image even with tissue transformation.

Figure 4A:
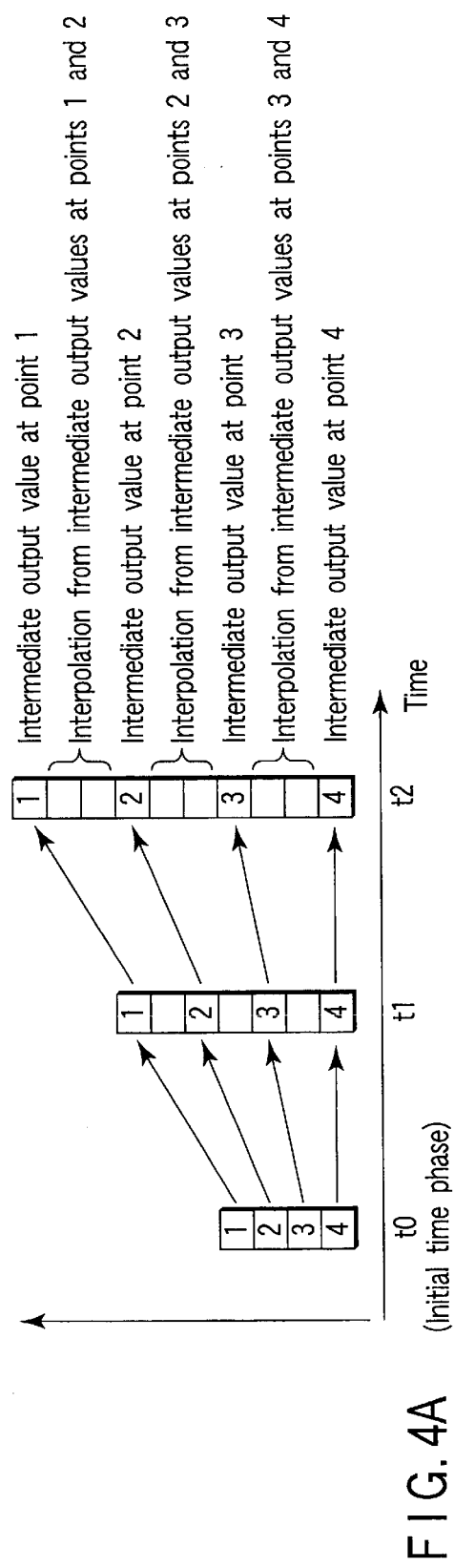
FIGS. 4A and 4B are conceptual views for explaining interpolation processing.
Figure 4B:
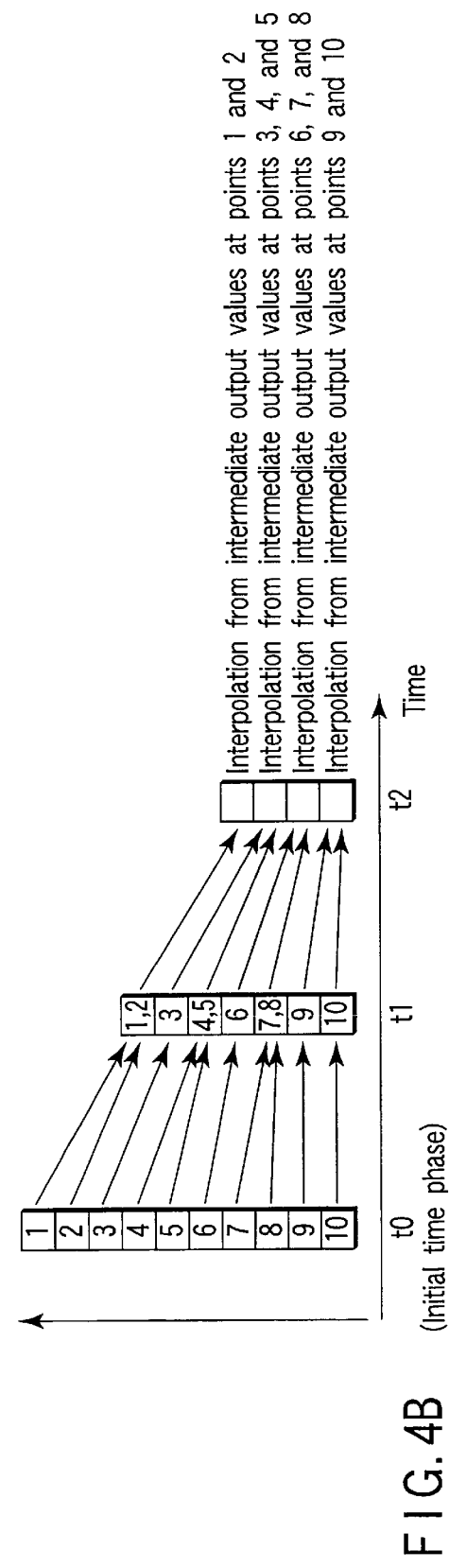

FIGS. 4A and 4B are conceptual views for explaining interpolation processing. As shown in FIG. 4A, when a short region expands in a motion direction at a computation start time phase, gaps are produced among the positions of tracking points. An appropriate value of each points in the gaps are therefore obtained by weighted addition processing using the values of a plurality of neighboring intermediate output points around this point (That is corresponding points in the predetermined time phase, which will be described after.). This weighting factor preferably increases with a decrease in the distance between a point of an output image and the position of a point of a plurality of target tracking points. Such processing can be regarded as a kind of interpolation processing, and hence will be simply referred to as interpolation.

In FIG. 4A, for example in time phase t2, the signal values of two points, each points being existed between a point 1 and a point 2, are interpolated by the intermediate output value in points 1 and 2. Alternatively, as shown in FIG. 4B, when the long region is getting shrunk in the computation start time phase, overlaps are produced among the positions of tracking points.

In the predetermined time phase, the appropriate signal value of the point corresponding to this overlap is calculated by the weighted addition processing using the values of overlapped intermediate output points (That is corresponding points in the predetermined time phase, which will be described after.).

According to this interpolation processing, a uniform output image can be estimated even with tissue transformation.

The detailed arrangement and function of an apparatus according to the first embodiment will be described in detail below. The first embodiment will exemplify the case wherein the heart is set as a target organ, and the local motion of a tissue of the myocardium is evaluated by using two-dimensional images.

Figure 5:
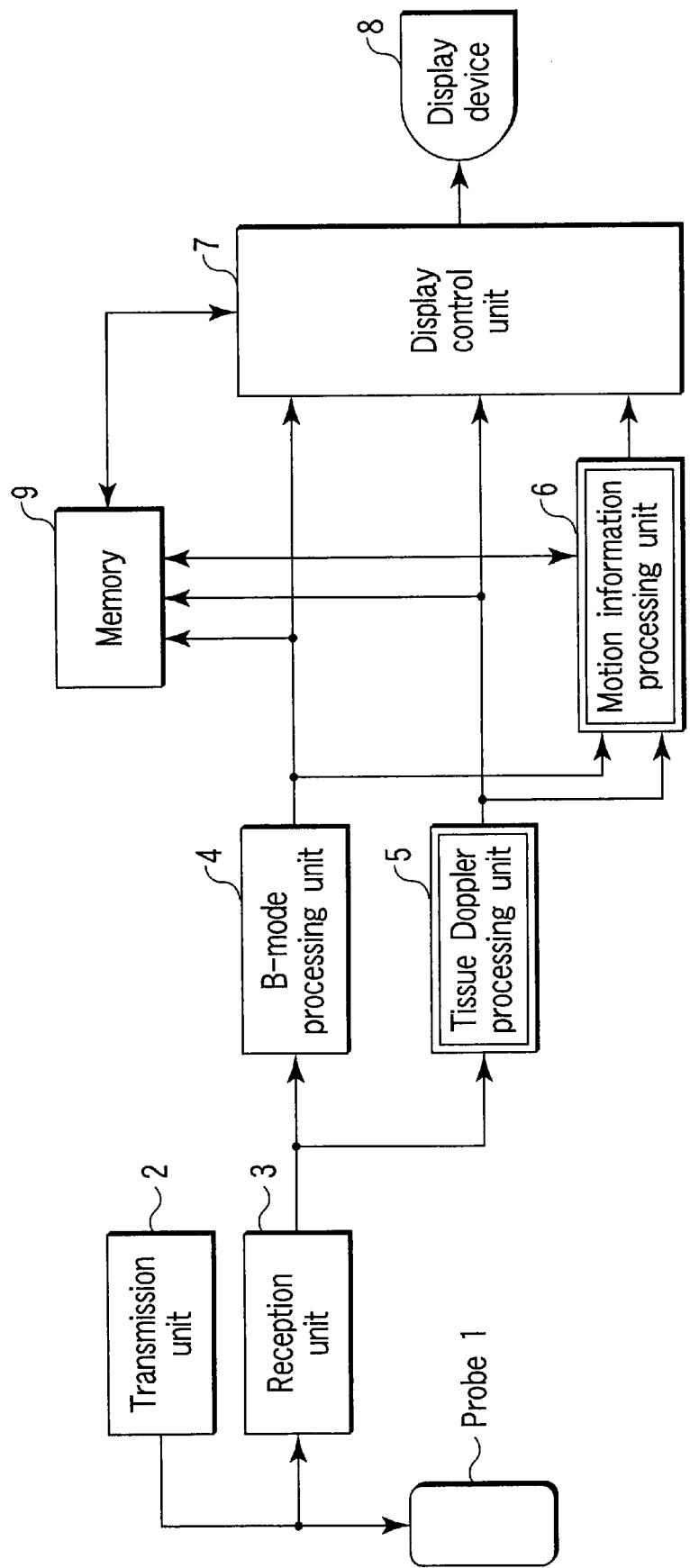
FIG. 5 is a block diagram showing the schematic arrangement of an ultrasound diagnostic apparatus according to the first embodiment.

FIG. 5 is a block diagram showing the arrangement of an ultrasound diagnostic apparatus according to the first embodiment. An ultrasound probe 1 includes an ultrasound oscillator array having a plurality of ultrasound oscillators arrayed, which convert electrical signals into ultrasound waves. Ultrasound waves are transmitted/received to/from an object to be examined by using this ultrasound oscillator array. Assume that in the first embodiment, the ultrasound probe 1 is a sector probe target for the heart.

A transmission unit 2 generates driving signals to transmit ultrasound waves from the ultrasound oscillator array. The transmission unit 2 generates a driving signal with a predetermined delay characteristic for each oscillator so as to form an ultrasound beam toward a predetermined scan line. A reception unit 3 generates an ultrasound echo signal corresponding to the predetermined scan line by performing delay addition processing for the ultrasound echo signal received by each ultrasound oscillator of the ultrasound oscillator array.

A B-mode processing unit 4 generates a B-mode signal corresponding to the amplitude strength of the ultrasound echo by performing envelope detection processing for the ultrasound echo signal having undergone the delay addition processing. The B-mode processing unit 4 also generates a B-mode ultrasound image representing a two-dimensional distribution on a predetermined slice of this B-mode signal. A tissue Doppler processing unit 5 obtains a tissue Doppler signal corresponding to the velocity, variance, and power of the tissue that is moving in the object on the basis of the Doppler deviation component of the ultrasound echo signal having undergone the delay addition processing by performing quadrature detection processing, autocorrelation processing, and the like. The tissue Doppler processing unit 5 also generates a tissue Doppler ultrasound image representing a two-dimensional distribution of the signal corresponding to the velocity, variance, and power value on a predetermined slice. A motion information processing unit 6 executes each of processes to obtain a motion information shown as FIG. 1A on the basis of the B-mode ultrasound image and Doppler ultrasound image output from the B-mode processing unit 4 and tissue Doppler processing unit 5. The specific action of the motion information processing unit 6 will be describes in detail later.

A display control unit 7 generates a display image on the basis of a B-mode ultrasound image, Doppler ultrasound image, and two-dimensional distribution image of displacements or strains. Examples of the display image are a superimposed image of a B-mode ultrasound image and a tissue Doppler ultrasound image and a superimposed image of a B-mode ultrasound image and a two-dimensional distribution image of displacements or strains. A display means 8 displays the display image generated by the display control unit 7.

A memory 9 stores ultrasonic images corresponding to time phases, distribution images of the motion velocities corresponding to time phases generated by the motion information processing unit 6 and the like.

The specific action of the motion information processing unit 6 shown in FIG. 1A will be described in detail below referring to FIGURES.

[Generation of Spaciotemporal Distribution Image of Corrected Velocities Based on Motion Field: Steps S1 and S2]

Figure 6B:
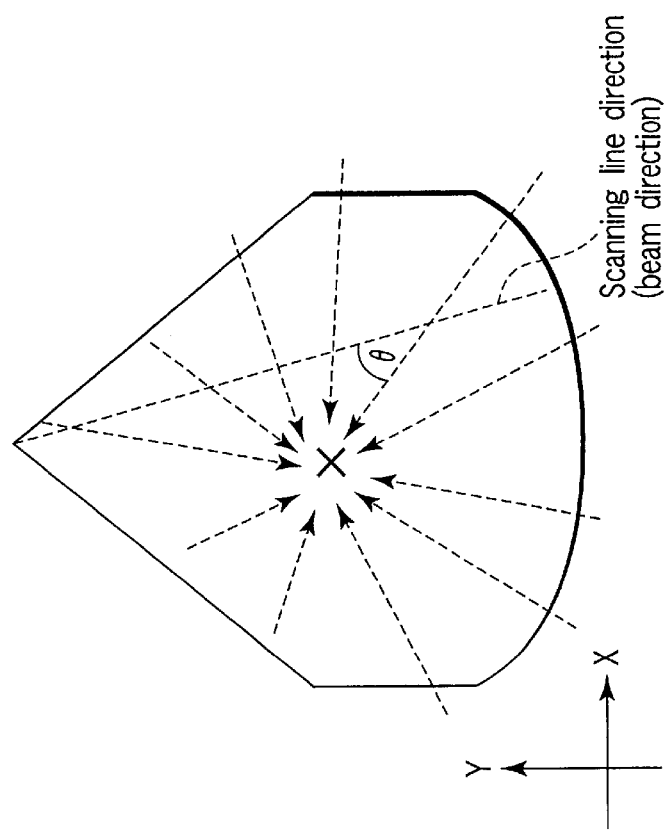
FIGS. 6A and 6B are conceptual views for explaining motion fields.
Figure 6A:
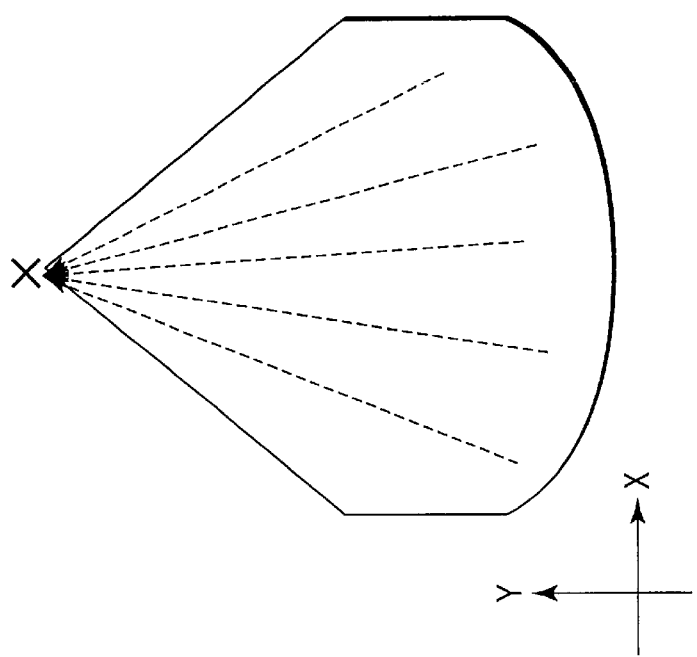

First of all, the motion information processing unit 6 obtains a spaciotemporal distribution image (two-dimensional distribution image in each of time phases) of velocities in the motion direction defined in a motion field. FIGS. 6A and 6B are views for explaining the definition of a motion field. FIG. 6A shows a raster motion field. FIG. 6B shows a contraction motion field. In FIGS. 6A and 6B, cross mark represents a center point of motion and array mark represents a direction of motion.

The raster motion field in FIG. 6A is a motion field expanding along each ultrasound beam direction for an ultrasound scan. The sign of a velocity becomes positive when the corresponding portion moves closer to the ultrasound probe 1, and becomes negative when the portion moves away from the ultrasound probe 1. As is well known, in such a raster motion field, letting θ be the angle (called the Doppler angle) defined by the actual motion direction and a velocity component in the ultrasound beam direction, the observation velocity estimated by the tissue Doppler method is represented by:

$$(\text{observation velocity}) = \cos\theta \ast (\text{actual motion velocity})(0° \leq \theta \leq 180°) \quad (7)$$

The dynamic state of the motion of a tissue of the heart is very complicated, and hence it is difficult to estimate all motions in the raster motion field. When an optimal short-axis plane for the evaluation of contraction/expansion in the thickness direction of the myocardium is to be evaluated, in particular, the ultrasound beam direction coincides with the motion direction in only a narrow range in the 12 o'clock direction (right above) when viewed from the contraction center where the ultrasound beam direction coincides with the motion direction. The ultrasound beam direction and motion direction are parallel but become opposite directions in the six o'clock direction when viewed from the contraction center.

In evaluating the motion of the myocardium in the contraction/expansion direction along the short axis, therefore, it is preferable that a motion field called a contraction motion field like the one shown in FIG. 6B be defined, and a corrected velocity be obtained assuming that a direction in the motion field coincides with the actual motion direction. In the contraction motion field, a virtual contraction center of the cardiac wall is set in an image, and a direction toward the virtual contraction center is defined as a motion direction. Note that the operator may manually set a virtual contraction center while seeing a displayed ultrasound image, or the apparatus may automatically set it on the basis of an ultrasound image by image analysis processing.

In the contraction motion field, velocity components approaching the virtual contraction center are obtained by equation (8) given below. The sign of a velocity becomes positive when the corresponding portion moves closer to the virtual contraction center, and becomes negative when the portion moves away from the center. A two-dimensional distribution image of corrected velocities obtained in correspondence with this contraction motion field is obtained. Note that this two-dimensional distribution image of corrected tissue velocities may be displayed on the display means 8, as needed.

$$(\text{corrected velocity}) = (\text{observation velocity})/\cos\theta((0° \leq \theta \leq 180°) \quad (8)$$

Next, display of limit range of tissue tracking imaging process will be described below. In the tissue Doppler method, such a motion field definition is indispensable for estimating the positions of tracking points to be described later. This is because the moving directions of the tracking points moving in a two-dimensional image are determined. If, however, the Doppler angle θ is near 90°, corrected velocities cannot be obtained with high reliability. In such a range (a range in the two or 10 o'clock direction in the case of a short axis), therefore, the evaluation of motion has its limit. In such a range with low reliability, a limit range of tissue tracking imaging is preferably displayed to make the user recognize it. It is also preferable that no velocity information as input information for processing be used in this limit range. In order to set this limit range, a predetermined limit Doppler angle is provided. This limit Doppler angle slightly varies due to the differences in tissue Doppler image quality among different objects to be examined (especially in the process of studying an optimal value in practice), and hence the user may be allowed to set an optimal value. The default limit Doppler angle is preferably set to, for example, 80° to 110°.

Note another effect of the display of this limit range. This display can indicate what kind of motion field is currently set in an image. For example, with regard to a single short-axis plane, a motion in the rotational direction (parallel to the contour of the myocardium) can be an evaluation target as well as a motion in the contraction/expansion direction (the main direction, and attention is often paid to it). If, therefore, a plurality of motion fields can be set, a third party can recognize what kind of motion field at a glance of an output image. In the case of a rotational motion field, unlike a contraction motion field, Doppler angle limit ranges appear near the 12 and six o'clock directions when a short-axis plane is to be generated.

Figure 7B:
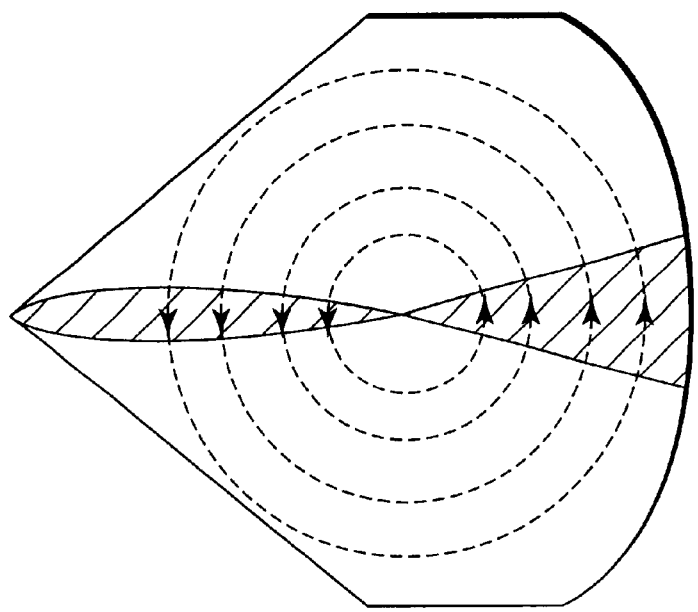
FIGS. 7A and 7B are views for explaining display examples of Doppler angle correction limit ranges.
Figure 7A:
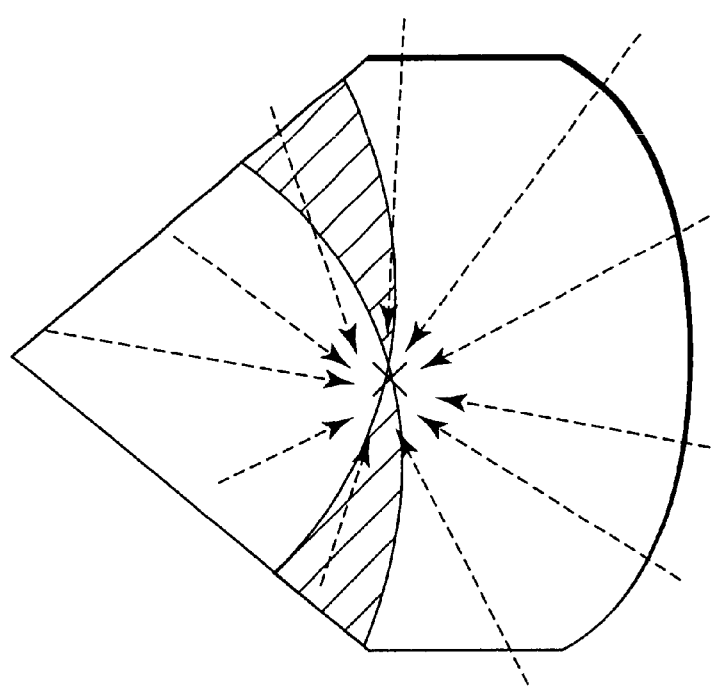

FIGS. 7A and 7B show examples of how motion fields and limit ranges are displayed. Specifically, FIG. 7A shows limit ranges in a contraction motion field. FIG. 7B shows limit ranges in a rotational motion field.

Referring to FIGS. 7A and 7B, the mark X representing a virtual contraction center, the arrows indicating motion direction in the defined motion fields, and the limit ranges are displayed. Each limit range is made to be recognized by a method of displaying lines on the boundary portions of the limit range, a method of making the color or luminance inside the limit range differ from that in the remaining portion, or the like. These images are so displayed on the display means 8 as to be superimposed on the above two-dimensional dilation processing image of corrected tissue velocities.

[Setting of Tissue Tracking Imaging Start Time Phase: Step S3]

Figure 8A:
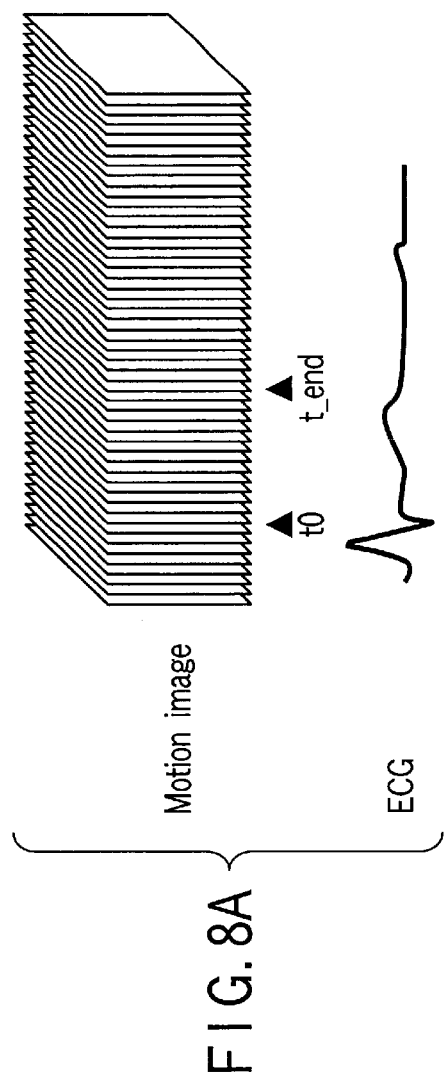
FIGS. 8A and 8B are conceptual views for explaining setting of computation intervals.

The user selects a processing start time phase t0 (That is "initial time phase t0") with respect to a series of tissue Doppler motion images from images stored in the memory while referring to an electrocardiogram. In this case, it is preferable that the user be allowed to select a processing end time phase (t_end) as well as the processing start time phase. This makes it possible to set a time phase interval of interest for evaluation with respect to a cardiac cycle can be set to a desired interval (see FIG. 8A).

Figure 8B:
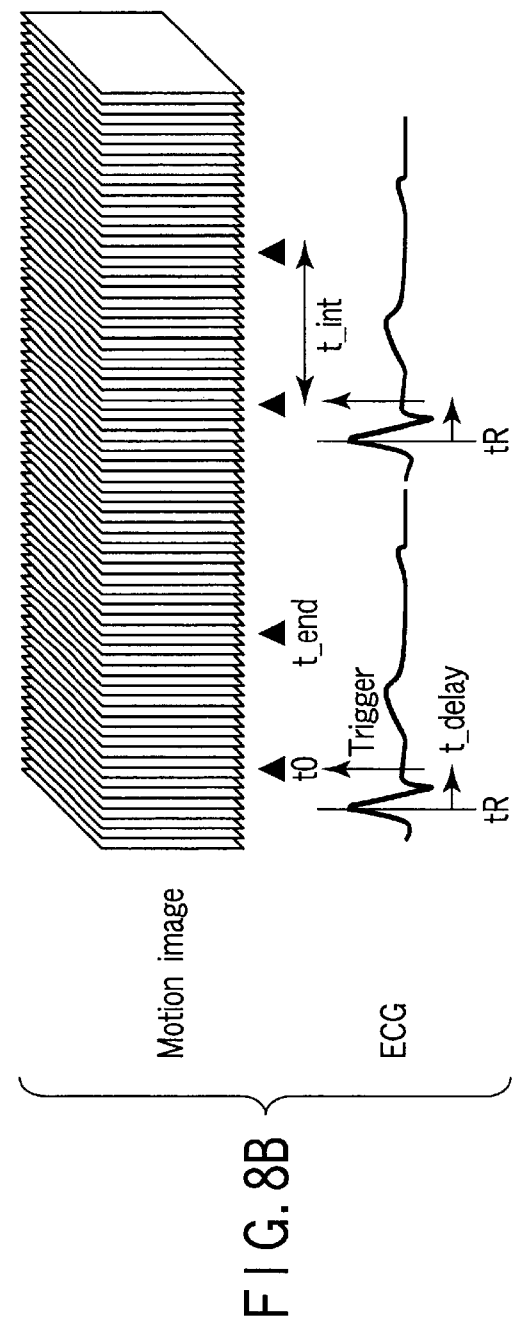

As shown in FIG. 8B, in acquiring motion images, a predetermined time phase (a time phase corresponding to tR+t_delay where tR is the time phase of an R wave; t_delay can be controlled and is called R wave synchronization when t_delay=0) trigger by an R wave of an electrocardiogram may be automatically set to t0 (That is "t0=tR+t_delay"). In this case, an interval corresponding to one cardiac cycle is preferably set such that the processing end time phase is set as the timing when the next trigger is produced. If a predetermined time interval (t_int) is set in advance from the start time phase, a time phase interval of interest for evaluation with respect to a cardiac cycle can be set to a desired interval as in the above case by setting this time phase of t0+t_int as an end time phase.

[Setting of Initial Time Phase and Tissue Range (Tracking Points) to be Tracked at Computation Start Time Phase: Steps S3 and S4]

The tracking points setting processing will be described in detail with reference to FIG. 9A.

FIG. 9A is a flowchart showing a flow of the groups of the tracking points setting processing. As shown in FIG. 9A, two-dimensional distribution data IM1 of corrected tissue velocities in an image range is obtained (step S1). Tracking processing may be started upon setting the range of all the two-dimensional distribution data as a target range. In the case of the heart, however, a range other than the tissue can also become a tracking target. For this reason, an image IM2 is generated, upon limiting only a range exceeding a controllable threshold as a tissue range, by using the luminance information of a B-mode signal (step S2). As a signal source used for such threshold determination, for example, the information of power that can be defined simultaneously with velocity information during tissue Doppler processing can be used as well as a B-mode signal. A B-mode signal or tissue Doppler power signal is information correlating with a signal intensity. In general, a tissue region is several 10 times higher in signal intensity than a blood flow region in the heart chamber, and hence such source is an effective means when ranges other than the tissue in the heart chamber are excluded from tracking targets. If a region (a shaded range in FIG. 9) selected as an effective range is displayed as a B-mode signal in setting a threshold, the user can set an optimal threshold while checking the selected tissue range.

Figure 9B:
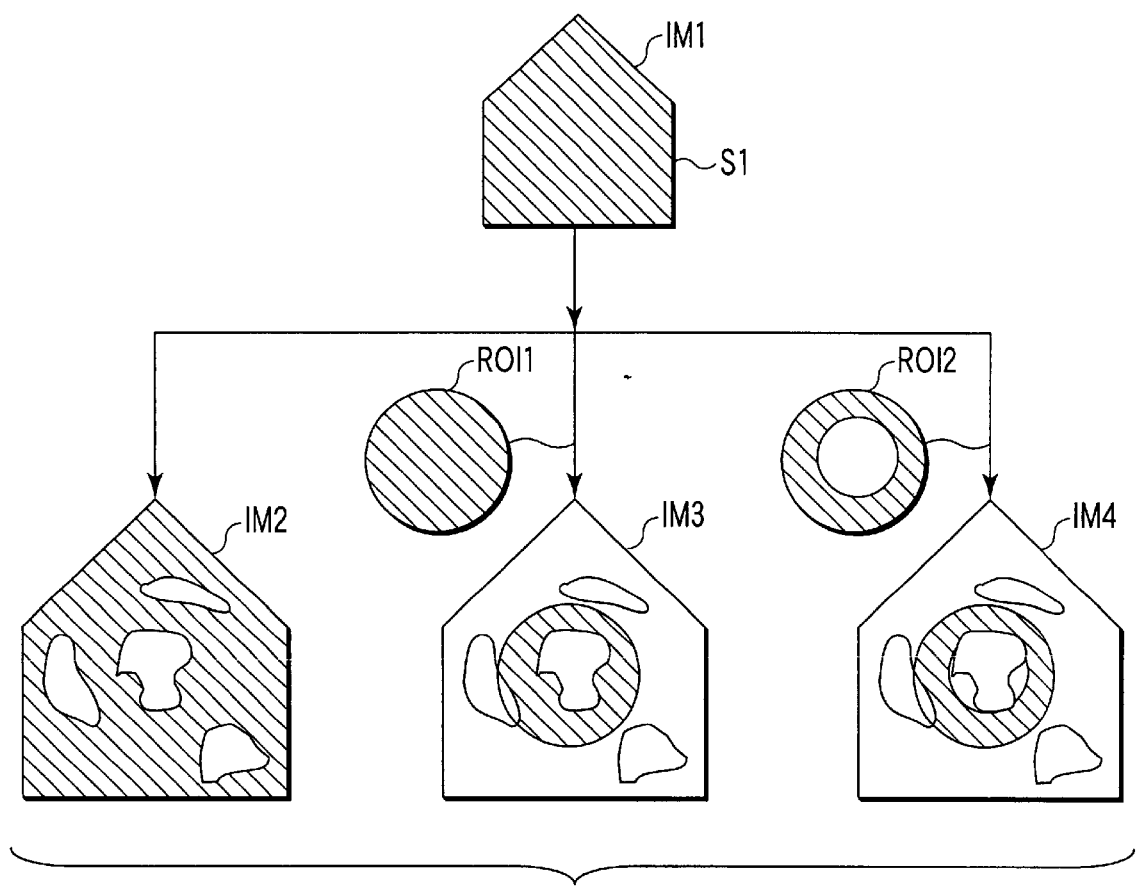
FIG. 9B is a conceptual view for explaining setting of a tracking target tissue range.

When a region of interest (ROI) is set in addition to the above manner of limiting a range, just a region exceeding a threshold which can be controlled and concerning with the ROI is extracted restrictively as a tissue range to generate the image IM3 and the image IM4 (step S4). This image generation by setting ROI technique is used to allow the user to extract only a myocardium range in a tissue range. In FIG. 9B, "IM3" indicates a case wherein an inner part of the short-axis epicardium is selected by using a circular ROI 1. "IM4" indicates a case wherein a portion between the short-axis epicardium and the endocardium is selected by using an ROI 2. For example, as shown in FIG. 9, by using such ROIs, this technique can be used to remove a range of the papillary muscle or remove a range in the heart chamber when no limitation is made by the above B-mode luminance. Since these ROIs are set to extract a myocardium tissue range, they can be used together with an ROI of the contour of the heart which is used to set the above motion field (the scheme used in MVG-S/L).

[Estimation of Moving Positions of Tracking Points at Each Time: Step S5]

The moving position of each point of the tracking points selected in the above manner in a series of motion image spaces (which is image spaces constructed by a plurality of ultrasonic images arranged in time ordering.) is estimated.

Assume that motion images are obtained at predetermined time intervals dt. As a motion field, a contraction motion field based on a virtual contraction center is set. For the sake of simplicity, assume that this virtual contraction center is fixed from the viewpoint of time phase, and the motion field is constant from the viewpoint of time phase.

As a method of estimating and tracking positions, a method like the TDT method is preferably used. According to the TDT method, when the one-dimensional space direction of the M mode (i.e., the beam direction) coincides with the motion direction, accurate tracking can be done. In the case of two-dimensional images, accurate tracking can be done by using a motion field direction and velocity components in this direction in the following manner.

First of all, letting Vc be a velocity component (corrected velocity) which a given one of the tracking points has, at the first time phase, in the motion direction at a position corresponding to the first time phase, a position (x, y) at the next time phase is estimated by:

$$(x, y) = (Vc*dt*\cos(th), Vc*dt*\sin(th)) \quad (9)$$

where th is the angle defined by the motion direction and the x-axis.

At the next time phase, Vc and th are obtained at the position (x, y), and the position at the next time phase is estimated by using equation (9). By repeating this step, the moving position of this point at each time phase is obtained.

As such methods of estimating moving positions in the future, several means are known in addition to the above method using only information at the current time phase. Such means include a means for estimating a moving position by using information at the current time phase and information at the next time phase in the future (Eular method: using the position in the future obtained in the above manner as temporary estimated position 1, further obtaining temporary estimated position 2 in the future on the basis of temporary estimated position 1 in the same process, and estimating a future position from the average of temporary estimated position 1 and temporary estimated position 2). Although the description of the details of these methods will be omitted, each method is designed to define a moving position by using velocity information Vc and monition direction information dt, and any estimating means can be used within this category.

Note that a point defined in an image space has a finite size. More specifically, at the first time phase, the position of a point can be defined on a grid on which points are reliably defined. However, the positions estimated at the subsequent time phases do not necessarily coincide with the grid. In such a case, therefore, the value of Vc is preferably obtained by interpolation from the value of Vc defined on the grid at a plurality of neighboring points around the estimated position.

[Definition of Input Signal of Motion Direction Component and Acquisition of Intermediate Output Points by Time Integration: Step S6]

An intermediate output with respect to motion information of a tissue is defined on the estimated positions of tracking points. When a displacement is to be obtained as motion information, an intermediate output of a displacement with respect to velocity components in the motion direction at each time phase is obtained on the positions of the tracking points by integrating the velocity components in the motion direction by equation (10) given below while tracing back the positions of the tracking points in the time phase direction, as described earlier.

$$\text{displacement}(x,y,\tau) = \Sigma Vc(x,y,\tau)*dt \quad (10)$$

where t0 is the first time phase, and t is the current time phase. Assume that the sum in the range of $t0 \leq \tau \leq t$ is calculated.

Likewise, when a strain is to be obtained, an intermediate output of an ideal strain with respect to velocity components in the motion direction at each time phase is obtained on the positions of the tracking points by integrating the velocity components in the motion direction by equation (11) given below while tracing back the positions of pairs of tracking points in the time phase direction, as described earlier. In this case, (xa, ya) represents one of a pair of the tracking points which is selected at the first time phase, and (xb, yb) represents the other point of the pair of the tracking points which is separated from the point (xa, ya) by a predetermined initial length L0 in the motion direction at the first time phase.

$$\text{Strain } (xa,ya,t)=[\Sigma Vc(xa,ya,\tau)*dt-\Sigma Vc(xa,ya,\tau)*dt]/L0 \qquad (11)$$

Assume that the sum in the range of $t0 \leq \tau \leq t$ is calculated.

The value of Vc used for such a displacement or strain computation is also preferably obtained by interpolation from the value of Vc defined on the grid at a plurality of neighboring points around an estimated position as in the case of the above position estimation.

[Estimation of Corrected Output Values by Interpolation, Generation and Display of Strain Image: Steps S7 and S8]

The processing in [7] will be described by exemplifying the case wherein a two-dimensional image is used will be described with reference to FIGS. 10A to 10C. First of all, an image range which defines an output image at the current computation time phase is determined, and an output value at each point in the image is then obtained in steps (1) to (5). Since time phases are constant, a description of the term of time will be omitted.

Figure 10A:
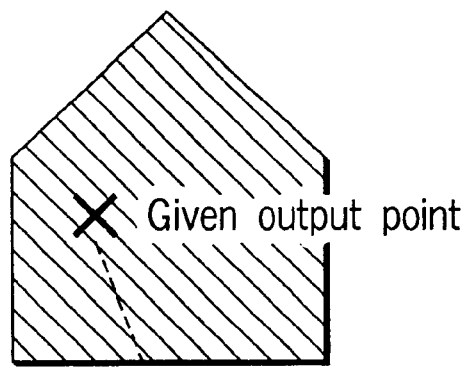
FIGS. 10A, 10B and 10C are conceptual views for explaining interpolation processing.
Figure 10B:
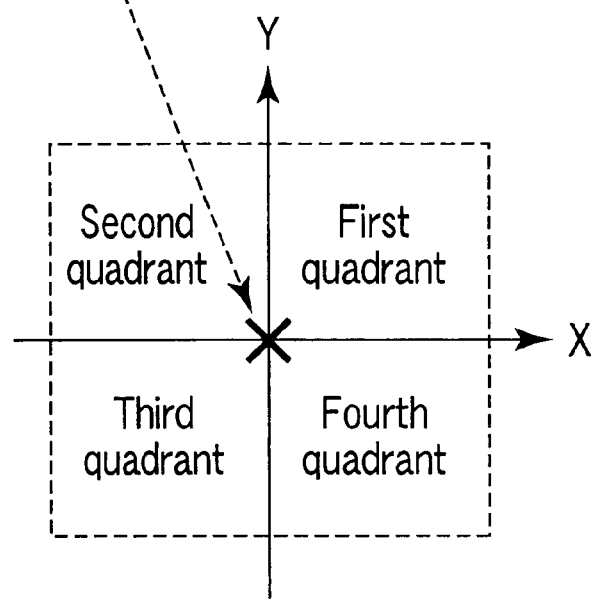

(1) In an output point in a predetermined time phase shown in FIG. 10A, as shown in FIG. 10B, search range which is centered on an output point and has a predetermined shape and size is set. This range preferably has a circular or square shape, and its size is set to, for example, about 5 mm.

Figure 10C:
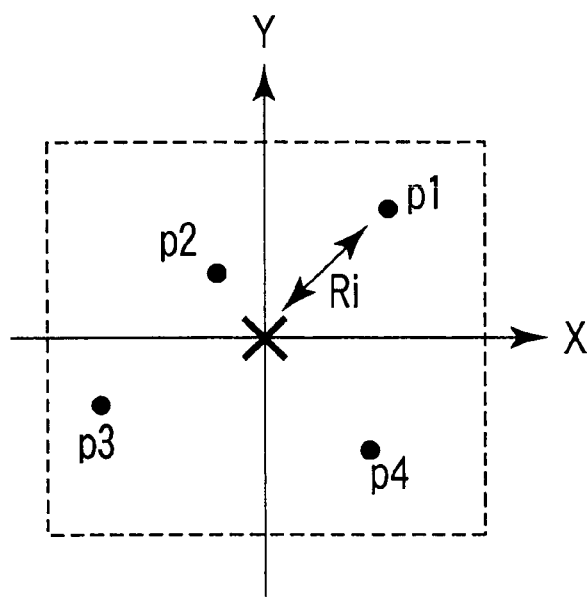

(2) As shown in FIG. 10C, the search range is divided into four quadrants, and each quadrant is searched for a tracking point pi (i=1 to 4) nearest to the output point.

(3) If no tracking point is found in any quadrant, the output is set to zero.

(4) If nearest tracking points pi are found in all the quadrants, an output is defined by equation (12) given below by using a distance Ri between pi and the output point and an intermediate output value M(pi) on pi.

$$\text{output} = \begin{cases} 1/\text{sum}*[1/R1*M(p1)+1/R2*M(p2)+1/R3*M(p3)+1/R4*M(p4)] & (R\text{min} > 0) \\ M(p\text{min}) & (R\text{min} = 0) \end{cases} \qquad (12)$$

wherein, Rmin is minimum value at each Ri, pmin is a point to obtain Rmin. Sum is a coefficient of weighting for normalization, sum=1/R1+1/R2+1/R3+1/R4.

(5) These steps are performed at all the output points to obtain an output image.

In the first embodiment, the weighting factor at each point pi is set to (1/Ri). However, this weighting factor may be defined by using other functions. For example, a function that increases in value with a decrease in the value of Ri is preferably used, which includes $(1/Ri)^{1/2}$ or Gauss function: $\exp(-\sigma Ri^2)$.

As described above, the displacement or strain image output through a series of steps is color-converted, and the resultant image can be displayed upon being superimposed on a B-mode image, as in the case of velocity display using a tissue Doppler image. A color map different from that for velocity is preferably used for such a motion information image of a tissue. More specifically, a color map having the following form is conceivable.

A myocardium portion that has expanded is displayed in red, whereas a myocardium portion that has contracted is displayed in blue. As the degree of the strain increases, the brightness of red or blue is increased (that is, when the strain has a positive value, it is displayed in red at a brightness corresponding to the degree, whereas when the strain has a negative value, it is displayed in blue at a brightness corresponding to the degree). At this time, a color bar indicating the relationship between the color, the brightness, and the expansion/contraction is preferably displayed together with the image.

Color map display need not always be performed in correspondence with both expansion and contraction (i.e., using both blur and red colors) as in the above manner, and may be selectively performed in correspondence with one of the states. It is preferable that the operator can select one of the display forms. When one of the states is to be selectively displayed, e.g., only the expansion of the myocardium is to be displayed, only the myocardium portion that expands is displayed in red at a brightness corresponding to the degree of strain. When only the contraction of the myocardium is to be displayed, only the myocardium portion that contracts is displayed in blue at a brightness corresponding to the degree of strain.

When both the expansion and contract of a region are to be displayed or one of them is to be displayed, the expansion and contract must be discriminated from each other and time phases must be correctly reflected. As a reference for this operation, ECGs (electrocardiograms) can be used.

Consider a case wherein the R—R interval of a short-axis plane of the heart is displayed as a strain image by the above color map display. In this case, in a systole, for example, only the expansion of the myocardium is displayed, and the manner in which the myocardium becomes thick is displayed in red. At this time, a signal indicating contraction may be determined as noise and erased. In a diastole, for example, only the contraction of the myocardium is displayed, and the manner in which the myocardium becomes thin is displayed in blue. At this time, a signal indicating expansion may be determined as noise and erased.

By visualizing the expansion/contraction of the myocardium on the basis of the computation time phases of strain and cardiac time phases by ECGs in this manner, information that is easy to see for the observer and useful for diagnosis and the like can be provided.

Note that the above color map display is realized by, for example, the display control unit 7. In addition, the above color map display is effective for, for example, displacement images as well as strain images. From the viewpoint of providing a user-friendly apparatus, for example, it is preferable that a short-axis plane (for thickening use) can be switched to a long-axis plane (for shortening use) by simple manual operation in the color map display setting, and the long-axis plane can be displayed in the same form as described above.

Figure 11A:
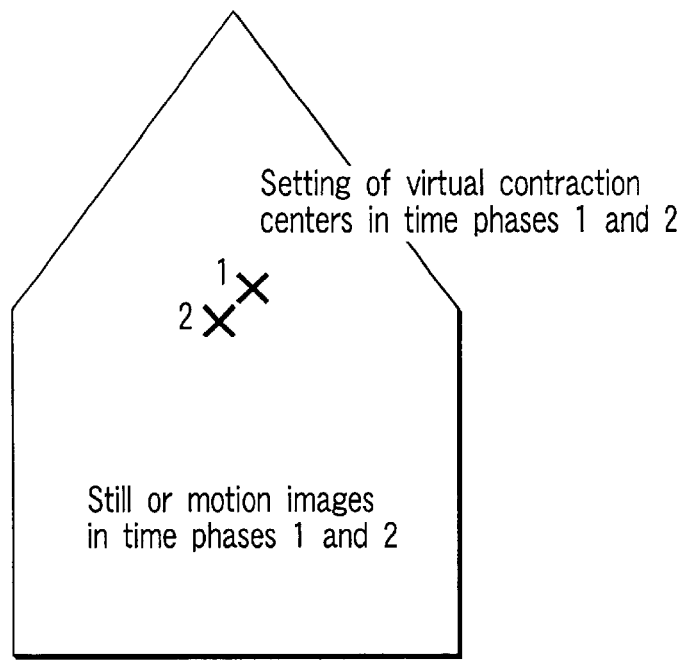
FIGS. 11A, 11B and 11C are views for explaining cases wherein a virtual contraction center is moved and set in terms of time phase.
Figure 11B:
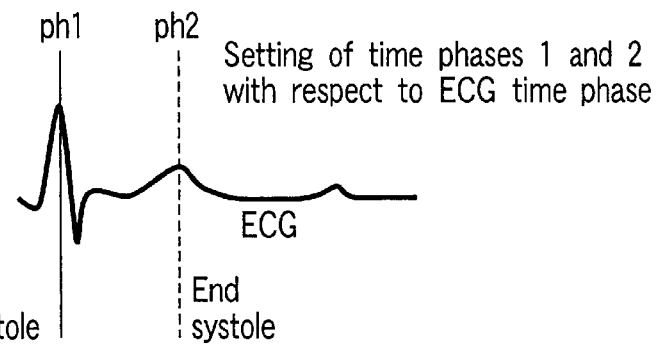
Figure 11C:
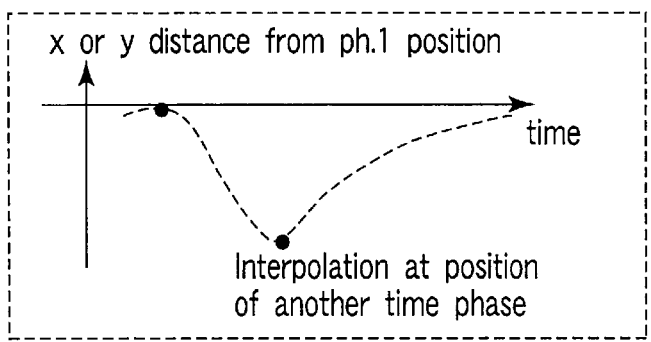

A modification of the first embodiment will be described next. According to the above description, for the sake of simplicity, a virtual contraction center is fixed. However, this center can be moved within a time phase in accordance with the movement of the contraction center position accompanying the movement of the heart. An example of such means for this operation is a scheme of making the user set virtual contraction centers in several specific time phases in a cardiac time phase and obtaining virtual contraction center positions in other time phases by interpolation between the time phases. As an interpolation function, a function that linearly estimates a center position from the positions set in the preceding and succeeding time phases or a function that simulates a predetermined motion is preferably set in advance. In the latter case, for example, as shown in FIGS. 11A, 11B and 11C, two characteristic time phases, i.e., an end diastole (time phase phi) and end systole (time phase ph2), are set, and virtual contraction center positions are set in these two time phases. All these means can be practically effective means for obtaining virtual contraction center positions matching the movement of the heart while saving the user the trouble of making settings as much as possible. This is because, if a scheme of making the user directly set virtual contraction centers at desired positions is used as a virtual contraction center setting method, the above operation can be realized by setting one point in each time phase.

On the other hand, in the conventional MVG-S/L method, a motion direction is defined by a contour. In a case of local ailment such as cardiac infarction, contracting/expanding motion toward a virtual contraction center does not always occur. In this method, an attempt is made to define this motion in a direction perpendicular to the contour. According to the MVG-S/L method, however, since contours must be set, it takes much labor and time for the user to set such contours in a plurality of time phases. Most ideally, such setting may be done by automatic contour tracking. Many attempts have made to realize such operation. Currently, however, an error factor dependent on ultrasound image quality has become a problem.

Figure 12:
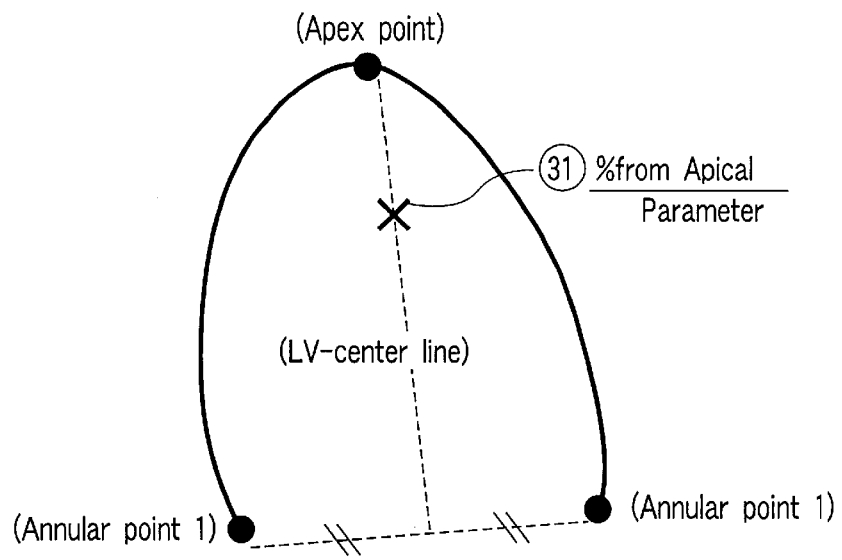
FIG. 12 is a view for explaining a case wherein a virtual contraction center is set from the anatomical position information of the heart.

When four- and two-chamber images from the apex of the heart are to evaluated, a virtual contraction center setting method like that shown in FIG. 12 may be used as an intermediate method among the above methods. For example, in THE TRANSACTIONS OF THE INSTITUTE OF ELECTRONICS, INFORMATION AND COMMUNICATION ENGINEERS, D-II Vol. J83-D-II No. 1, pp. 183–190 (January 2000), "Ultrasound Cardiac Wall Dynamic Contour Extraction Method Using Partial Shape Restraint Contour Model" is described. According to this method, it has been reported that automatic tracking can be done for an annular portion by a pattern matching means by using the characteristic structure of the annular portion. By designating three points, i.e., two points on the annular region and one point on the apical portion that hardly moves in an image, a predetermined point on the LV-center line in FIG. 12 is set as a dynamic virtual contraction center. In Circulation 61: 966–972, 1980, "Evaluation of methods for quantitating left ventricular segmental wall motion in man using myocardial markers as a standard", is described. According to this method, this virtual contraction center is preferably set as an initial setting at a 31% position with respect to the apex of the heart.

A processing method in a case wherein a dynamic contraction motion field is set by these means will be described below. This processing is associated with the steps S5 of [Estimation of Moving Positions of Tracking Points at Each Time] and S6 of [Definition of Input Signal of Motion Direction Component and Acquisition of Intermediate Output Points by Time Integration].

Figure 13A:
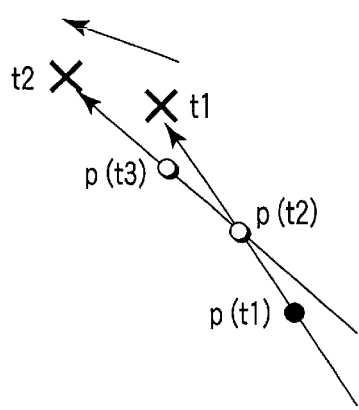
FIG. 13A is a conceptual view for explaining tracking in a dynamic motion field.
Figure 13B:
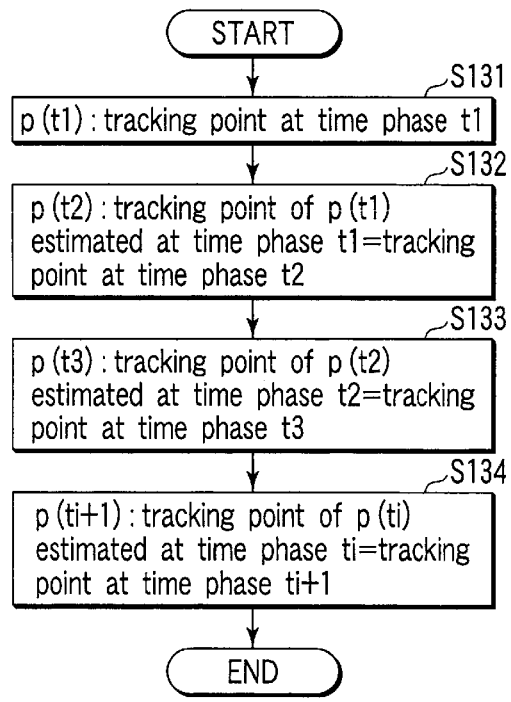
FIG. 13B is a flowchart showing a flow of the tracking processing in the dynamic field.

The basic steps in the case of the dynamic motion field do not greatly differ from those in the case of the static motion field described above. This state will be described with reference to FIGS. 13A and 13B. The values Vc and th at the position (x, y) at time phase $t_i$ are required for the estimation of a tracking position at time phase $t_{i+1}$. These values may be obtained in accordance with the motion direction set in a given time phase; no problem arises even if the motion direction changes every time phase. For example, referring to FIG. 13A, the estimated position of p(t2) is moved onto the motion direction at t1 by applying th determined by the motion direction at t1 and Vc corrected by the direction to p(t1), and the position of p(t3) is estimated on the motion direction at t2 by applying th determined by the motion direction at t2 and Vc corrected by the direction to p(t2) (Step S133 in FIG. 13B). This step is repeated (Step S134 in FIG. 13B). Note that the same procedure is executed regardless of whether the motion direction does not change between t1 and t2.

Obviously, different computation results may be obtained depending on whether the motion direction changes or does not charge between t1 and t2. This difference is associated with an error in terms of which matches with the true motion of the tissue better. When the true motion direction changes in terms of time phase, an improvement in an error with respect to a tracking position can be expected by changing the motion direction in accordance with this change.

Likewise, with regard to an input signal in a case wherein an intermediate output is to be obtained, Vc corrected by the motion direction determined by the time phase t is used as in the above equation definitions.

(Second Embodiment)

In the second embodiment, tissue tracking imaging is performed by two-dimensional image pattern matching. FIG. 14 is a block diagram showing the arrangement of an ultrasound diagnostic apparatus according to the second embodiment. This embodiment differs from the first embodiment in the arrangement associated with a moving vector processing unit 13 and motion information processing unit 6. Since the arrangement of the remaining part is the same as that of the first embodiment, a description thereof will be omitted.

The moving vector processing unit 13 detects the moving position of a tissue by performing pattern matching between two ultrasound images in different time phases, and obtains a tissue velocity on the basis of this moving position. More specifically, the moving vector processing unit 13 extracts a partial image from the first ultrasound image and obtains the position of a portion of the second ultrasound image which exhibits the highest similarity to the extracted partial image. The moving vector processing unit 13 then obtains the distance between this position in the second ultrasound image and the position of the partial image in the first ultrasound image, and divides the distance by the time difference between the first and second ultrasound images, thereby obtaining the moving velocity of the tissue. By performing this processing for each point in the ultrasound image, the two-dimensional distribution data of tissue moving velocities can be obtained.

The motion information processing unit 6 obtains a two-dimensional distribution image of displacements or strains on a predetermined slice on the basis of the two-dimensional distribution data of tissue velocities output from the moving vector processing unit 13.

Figure 14B:
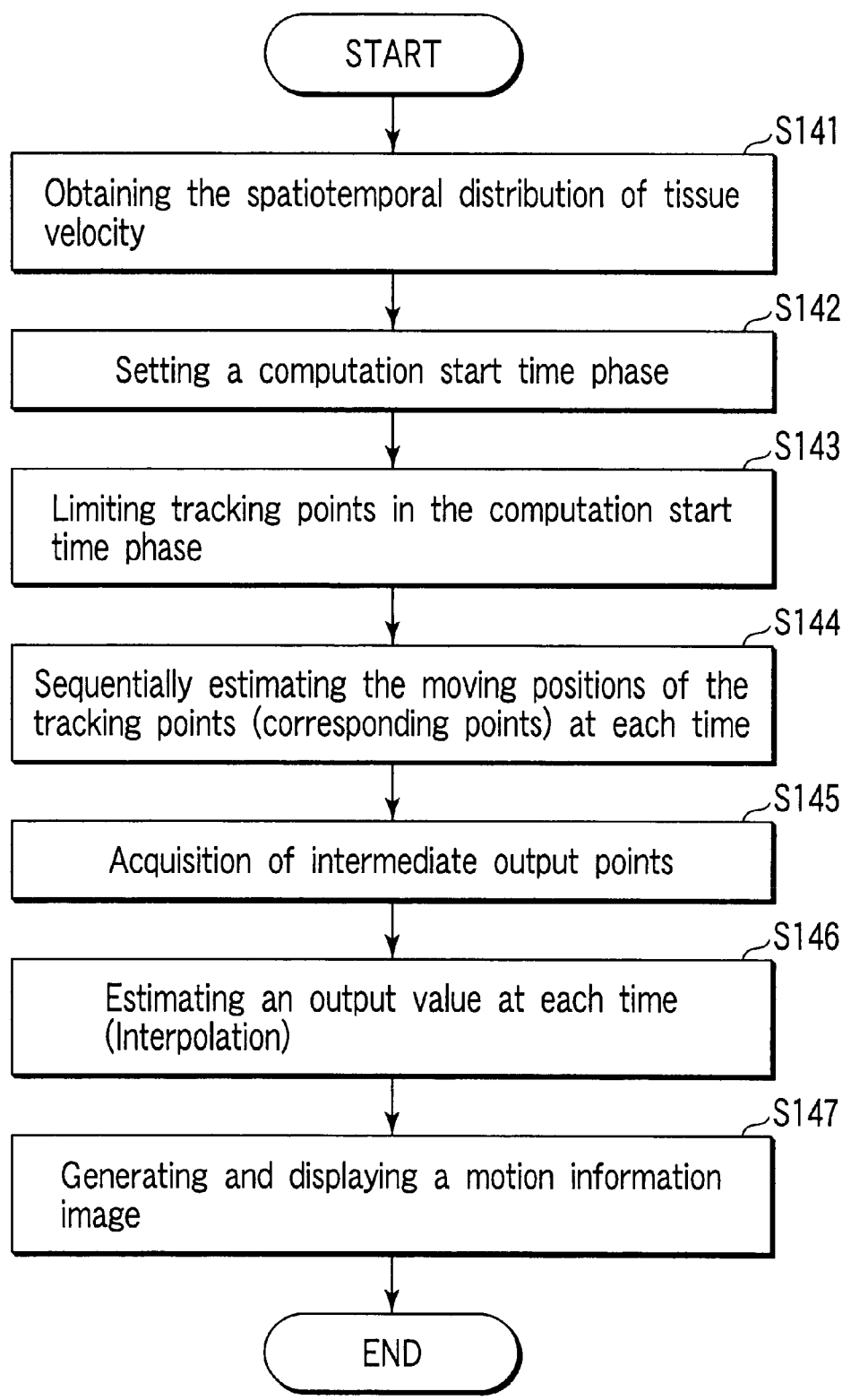
FIG. 14B is a flowchart showing a flow of the motion information image acquisition processing executed by the ultrasonic diagnostic apparatus according to the first embodiment.

In order to actually obtain a motion information image in the ultrasonic diagnostic apparatus according to the second embodiment, the following processes are executed as shown in FIG. 14B:

[1] (Step S141) acquisition of a spatiotemporal distribution image (Velocity-Field:VF) of tissue velocity;

[2] (Step S142) setting a computation start time phase;

[3] (Step S143) limiting an area (tracking points) of the tissue to be tracked in the computation start time phase;

[4] (Step S144) sequentially estimating the moving positions of the tracking points at each time by using VF (using also MF in the tissue Doppler method) time intervals;

[5] (Step S145) defining an input signal by using MF at each point of the tracking points and performing integration up to each time (acquisition of intermediate output points); and

[6] (Step S146) estimating an output value at each time and each point of an output image by using the value of the nearest intermediate outputs.

[7] (Step S147) generating and displaying a motion information image

[Acquisition of Tissue Velocity]

A spatiotemporal distribution image of tissue velocities is obtained by the moving vector processing unit 13 designed to perform processing such as the pattern matching technique described with reference to cross-correlation coefficient display in Jpn. Pat. Appln. KOKAI Publication No. 8-164139. With pattern matching, a moving position can be estimated at each point per time phase interval dt from the current time phase to the next future time phase, and hence a two-dimensional tissue velocity is defined at each point by dividing the estimated position by dt.

The second embodiment has advantages over the first embodiment. First, there is no Doppler angle limit. Second, a tracking position can be obtained without any assumption of a motion field (without causing the operator or the like to set a motion field) because a two-dimensional moving vector is directly estimated. On the other hand, in order to improve the spatial resolution of velocity estimation, a long computation time is required.

Figure 15B:
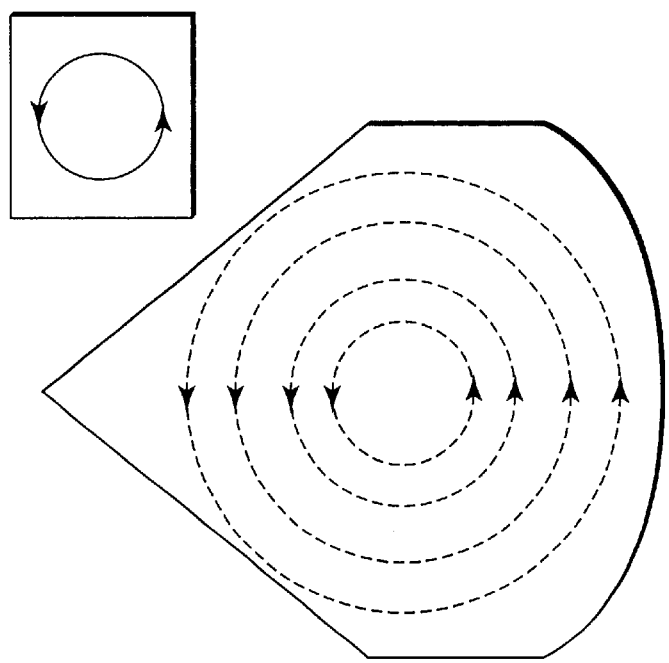
FIGS. 15A and 15B are views showing display examples associated with setting of motion fields.
Figure 15A:
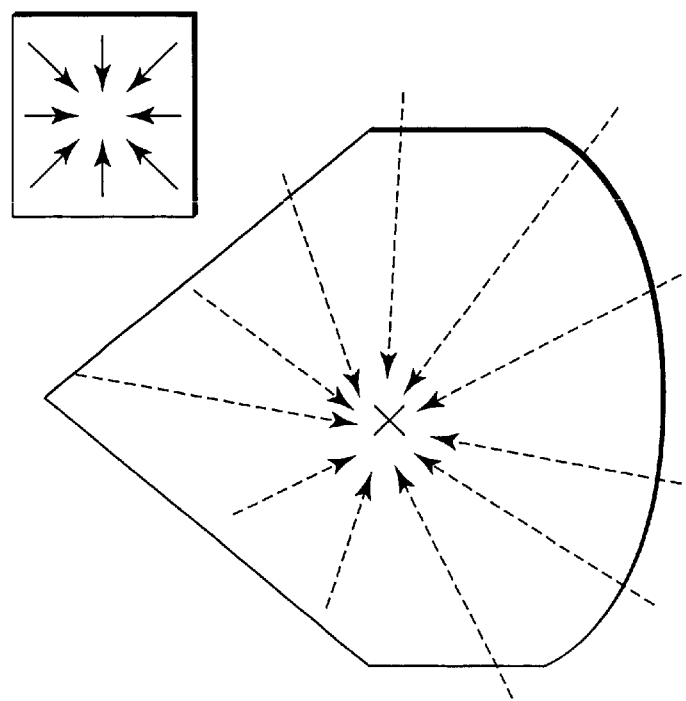

Note that, in the second embodiment, therefore, the setting of motion field is unnecessary for the setting of the tracking points. However, in this case, as shown in FIGS. 15A and 15B, it is preferable that a motion field definition is used to obtain only a desired motion information component in a desired motion direction. This idea is similar to that of the definition of an input signal of a motion direction component in the first embodiment.

The purpose of obtaining only a desired motion information component is to obtain a result that can be understood more easily by reducing the number of dimensions of information amount and providing an output value specified for only a motion direction component of interest as an image. If two-dimensional tissue velocities are used, two-dimensional displacements and strains can be defined. Even if, however, this information is color-converted and superimposed on a two-dimensional B-mode image, the resultant display is difficult to understand in practice. For example, the information of an intended motion direction component can be clearly understood by extracting only a component in the direction of a virtual contraction center and performing color display similar to that in the first embodiment rather than the above operation. When a component in another motion direction is to be evaluated, another motion field (e.g., a motion direction perpendicular to a contraction motion field; a rotational motion field in the case of a short axis) may be set to obtain an output image, thus separating evaluating components in the respective motion directions.

In the second embodiment, since there is no Doppler angle limit, setting and display of limit ranges as in the first embodiment are not required. Since no limit ranges are displayed, in order to make a third party recognize a set motion field, the set state of the motion field must be explicitly displayed. In this case, as shown in FIGS. 15A and 15B, the motion field is indicated by an icon.

[Setting of Tissue Tracking Imaging Start Time Phase and Setting of Tissue Range (Tracking Points) to Be Tracked in Computation Start Time Phase: Steps S142 and S143]

These settings are the same as those in the first embodiment.

[Estimation of Moving Positions of Tracking Points at Each Time: Step S144]

The positions of tracking points in the next time phase can be obtained by multiplying two-dimensional tissue velocities in the current time phase by a time phase interval dt.

[Definition of Input Signal of Motion Direction Component and Acquisition of Intermediate Output Points by Time Integration: Step S145]

The difference in this point between the first and second embodiments will be described below.

Figure 16:
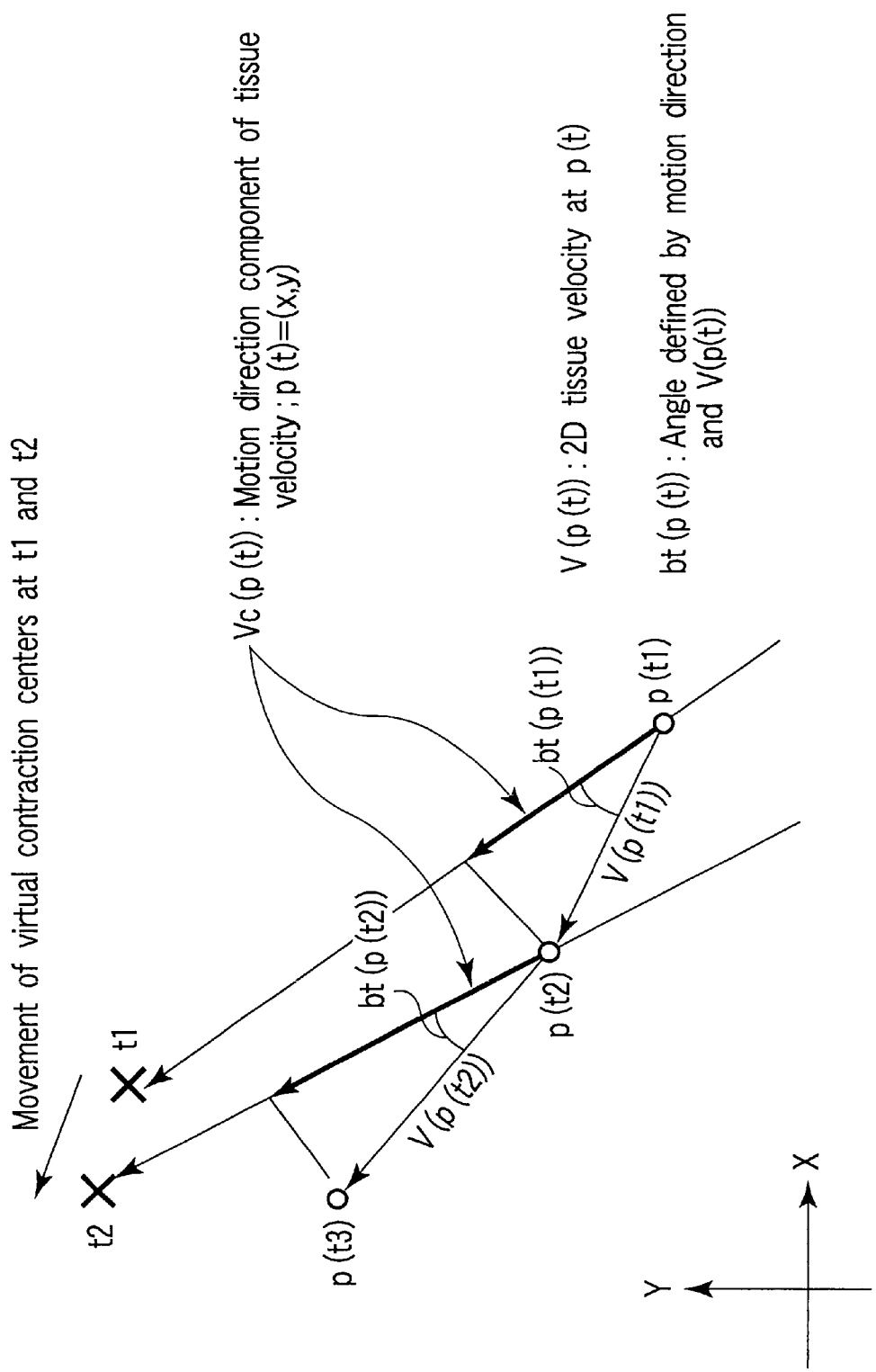
FIG. 16 is a conceptual view for explaining a velocity definition by using motion direction components in the second embodiment.

The positions of tracking points may be tracked by tracing positions p(t) of the tracking points in each time phase t described above. The tissue velocities at these positions are two-dimensional, and have unique directions in the respective time phases. Therefore, as shown in FIG. 16, a velocity Vc(p(t)) of a motion direction component which is equivalent to Vc(x, y, τ) in the first embodiment is obtained by $$Vc(p(t)) = |V(p(t))| * \cos[bt(p(T))] \tag{13}$$

where bt(p(t)) is the angle defined by the motion field direction set at the position p(t) in each time phase and the direction of the tissue velocity.

It suffices if a computation similar to that in the first embodiment is performed by using this angle-corrected velocity component. In the case shown in FIG. 16, for the sake of generality, the motion direction dynamically changes. As described in the first embodiment, however, even in this case, processing definitions can be made.

[Estimation of Corrected Output Values by Interpolation, Generation and Display of Strain Image: Steps S146 and S147]

This processing is the same as that in the first embodiment.

By the above procedure, output image display can be realized in the second embodiment.

An example of the application of the output obtained by tissue tracing imaging according to the present invention to temporal analysis will be described next. As described with reference to a computation interval in the first embodiment, output images in a plurality of time phases are basically provided. Therefore, various temporal analyses can be easily applied by using the output images in this series of time phases. A main temporal analysis is associated with a curve representing a change in the motion information of a local region over time and display of an arbitrary M mode (also called curved-M).

[Curve Representing Change Over Time and Application of ROI Tracking Technique]

If the practical example of temporal analysis using ROI tracking based on Jpn. Pat. Appln. KOKAI Publication No. 10-151133 is applied to the present invention, a curve representing a change in tissue motion information such as displacement or strain over time is provided while the position of a local ROI set on an image is matched with the position of the myocardium, thus improving the utility of the information in terms of diagnosis. Note that as a means for moving the ROI position, the practical example described when a setting in a motion field is changed or the practical example of automatic tracking using velocity information which is described in the tissue tracking image step may be used.

[Curved-M Mode Analysis Application]

If the concept of development display disclosed in Jpn. Pat. Appln. KOKAI Publication No. 6-285065 is applied to the present invention, an arbitrary M-mode image of tissue motion information such as displacement or strain is obtained, and which segment of the myocardium exhibits a characteristic sick state of motion can be identified at a glance with some contrivance to a color map because this segment can be temporally compared with other segments, thus improving the utility of the information in terms of diagnosis. For example, the color map is preferably devised to alternately assign complementary colors. In this case, it is expected that a region with poor motion and a region with normal motion can be effectively and easily identified by setting proper strain and displacement values in the output range of the map.

According to the above arrangement, even if a target tissue is in motion, displacements or strains at a local region of the tissue are consecutively visualized within a series of time phase intervals by performing integration while tracking each moving position of the tissue. As compared with the prior art, with the effect of integration, a distribution image using information such as displacement or strain information whose stability is improved can be obtained. Take, for example, the heart. The difference in motion between the endocardium and epicardium coats of the myocardium can be grasped at a glance. In addition, since these motion information images are consecutively obtained within a time phase interval, the information can be easily applied to temporal analysis.

The present invention has been described on the basis of the embodiments. However, those who skilled in the art can make various modifications and corrections of the embodiments within the spirit and scope of the invention, and hence it should be understood that such modifications and corrections fall within the range of the present invention. For example, the embodiments can be variously modified within the spirit and scope of the invention as indicated by (1) to (3) below.

(1) For example, the above embodiments have exemplified the case wherein reception signals are obtained in a two-dimensional space. However, by dimensional expansion, a similar procedure can be applied to a case wherein reception signals are obtained in a three-dimensional space.

(2) The above procedure may be done by a general-purpose personal computer, workstation, or the like independently of the ultrasound diagnostic apparatus. In addition, a series of outputs associated with the present invention can be applied to the analysis of a soft tissue such as the liver and blood vessel walls as well as the heart.

(3) A virtual contraction center is set in the generation of a two-dimensional distribution image of velocities based on a motion field in the above embodiments. However, the virtual contraction center set in this manner may deviate from the actual contraction center.

In consideration of this point, the embodiments may be configured such that a virtual contraction center is set by the operator or automatically, two-dimensional distribution images centered on neighboring points (preferably a plurality of points) around the set virtual contraction center which are automatically set as remaining virtual contraction centers are obtained, and these images are combined. By using this composite image, the influence of a deviation between the virtual contraction center and the actual contraction center can be canceled out. In addition, the limit range for angle correction can be reduced in the first embodiment.

Note that if the above remaining virtual contraction centers fall outside the limit range, it is preferable that the remaining virtual contraction centers be not used and new virtual contraction centers be set.

What is claimed is:

1. An ultrasonic diagnostic apparatus comprising:

a memory which stores a plurality of ultrasonic images which corresponds to a plurality of time phases and are concerning with an object;

a distribution image generation unit configured to generate a plurality of distribution images of motion velocities in the plurality of the time phases on the basis of the plurality of the ultrasonic images;

a tracking point setting unit configured to set tracking points in a tissue range of the object in an image which is one of the plurality of ultrasonic images and corresponds to a predetermined time phase;

an estimation unit configured to estimate corresponding points which correspond to the tracking points in the plurality of ultrasound images corresponding to remaining time phases other than the predetermined time phase, on the basis of the plurality of distribution images of motion velocities;

a signal value determining unit configured to determine signal values at the tracking points and the corresponding points in each of the plurality of the time phases according to stretch of the tissue range of the object;

a motion information image generating unit configured to generate a motion information image on the basis of the signal values at the tracking points and the corresponding points; and a display unit configured to display the motion information image.

2. The ultrasonic diagnostic apparatus according to claim 1, wherein said distribution image generation unit includes:

a motion field setting unit configured to set a motion field which defines a motion direction of a tissue of the object; and a distribution image acquisition unit configured to acquire a distribution image of motion velocities toward the motion direction defined by the motion field in each of the time phases on the basis of the plurality of the ultrasonic imaging.

3. The ultrasonic diagnostic apparatus according to claim 2, wherein the motion field is vector field which converges to one point in an ultrasonic image.

4. The ultrasonic diagnostic apparatus according to claim 2, wherein the motion field is a predetermined vector field determined by anatomical position information of a tissue in each of the time phases.

5. The ultrasonic diagnostic apparatus according to claim 2, wherein the motion field is set in accordance with motion of a region of interest of the tissue in each of the time phases.

6. The ultrasonic diagnostic apparatus according to claim 2, wherein said display unit displays information representing at least one of a type and state of the set motion field.

7. The ultrasonic diagnostic apparatus according to claim 2, wherein said signal value determining unit determines displacement of at least the corresponding point in a latest time phase by accumulating velocities of the corresponding points corresponding to at least the tracking points in each of the plurality of the time phases and by time-integrating the velocities on the distribution images of motion velocities corresponding to the plurality of the time phases; and said motion information image generating unit generates a displacement image as a motion information image on the basis of the displacement of at least the corresponding point in a latest time phase.

8. The ultrasonic diagnostic apparatus according to claim 2, wherein the tracking points are set as a plurality of pair-points each of which is separated from each other by a initial length;

said signal value determining unit calculates a distance between the motion field direction components of each of the pair-points in each of the time phases while temporally tracking positions of each of the pair points, and generates signal values of strains at each of the pair-points separated from each other by the initial length by dividing the distance between the motion field direction components by the predetermined initial length, and said motion information image generating unit generates a strain image as a motion information image on the basis of the signal values of the strains.

9. The ultrasonic diagnostic apparatus according to claim 2, wherein said distribution image generation unit acquires a distribution image of the motion velocities by a tissue Doppler method, and said estimation unit estimates corresponding points corresponding to the tracking points in each of the time phases on the basis of at least motion velocities toward the motion direction, of the motion velocities at the tracking points, and an interval between the plurality of time phases.

10. The ultrasonic diagnostic apparatus according to claim 2, further comprising:

a Doppler angle setting unit configured to set an upper or lower limit of Doppler angles for obtaining motion velocity components toward the motion direction of the tissue, and said display unit displays the set upper or lower limit of the Doppler angles simultaneously with the motion information image.

11. The ultrasonic diagnostic apparatus according to claim 1, wherein said distribution image generation unit generates distribution images of the motion velocities by a pattern matching technique between two ultrasonic images in different time phases; and said estimation unit estimates corresponding points corresponding in each of the remaining time phases on the basis of the distribution images and an interval between the plurality of time phases.

12. The ultrasonic diagnostic apparatus according to claim 1, wherein, in the case where a first corresponding point and a second corresponding point in a predetermined time phase overlap at a third corresponding point in a succeeding time phase, said signal value determining unit determines a signal value of the third corresponding point on the basis of at least a signal value of the first corresponding point and signal value of the second corresponding point.

13. The ultrasonic diagnostic apparatus according to claim 1, wherein, in the case where a first tracking point and a second tracking point in an initial time phase overlap at a third corresponding point in a succeeding time phase, said signal value determining unit determines a signal value of the third corresponding point on the basis of at least a signal value of the first tracking point and signal value of the second tracking point.

14. The ultrasonic diagnostic apparatus according to claim 1, wherein said signal value determining unit determines signal value of a point which is in a tissue range and adjacent to the corresponding points, on the basis of at least a signal value of a nearest corresponding point.

15. The ultrasonic diagnostic apparatus according to claim 1, wherein said signal value determining unit determines signal value of a point which is in a tissue range and adjacent to the corresponding points, on the basis of at a signal value of a weighted corresponding point.

16. The ultrasonic diagnostic apparatus according to claim 1, wherein said signal value determining unit sets a predetermined search range in each of the plurality of the ultrasonic images on the basis of first point in a tissue range except for the corresponding points;

searches for the corresponding point which exists in the search range, determines a signal value of the first point in the tissue range on the basis of at least a signal value of a nearest corresponding point, when the corresponding point are searched out in the search range; and determines a signal value of the first point in the tissue range to 0 when the corresponding point are not searched out in the search range.

17. The ultrasonic diagnostic apparatus according to claim 1, wherein said display unit displays the tissue range according to a stretch of the tissue as an image by a color map display.

18. The ultrasonic diagnostic apparatus according to claim 1, further comprising:

a function acquisition unit configured to acquire a function of a change in tissue motion information over time in an arbitrary range on the motion information images on the basis of the motion information images, and wherein said display unit displays the function.

19. The ultrasonic diagnostic apparatus according to claim 1, wherein said motion information image generating unit generates M-mode image concerning with predetermined motion information in association with a position on an arbitrary curve or straight line determined by a user as the motion information image.

20. The ultrasonic diagnostic apparatus according to claim 1, wherein said tracking point setting unit sets a threshold for information correlated with intensity in each point of each of the plurality of the ultrasonic images; and sets the tracing points on the basis of determination as to whether the information correlated with the intensity is larger than the threshold.

21. The ultrasonic diagnostic apparatus according to claim 1, wherein said display unit displays the tracking point set by said tracing point setting unit.

22. The ultrasonic diagnostic apparatus according to claim 1, wherein said tracking point setting unit sets the tracking point in a region of interest set in the ultrasound image in the predetermined time phase.

23. The ultrasonic diagnostic apparatus according to claim 22, further comprising: region-of-interest setting unit configures to set the region of interest manually.

24. The motion information image generating method according to claim 1, wherein:

the generating the distribution image includes:

setting a motion field which defines a motion direction of a tissue of the object; and acquiring a distribution image of motion velocities toward the motion direction defined by the motion field in each of the time phases on the basis of the plurality of the ultrasonic imaging.

25. The motion information image generating method according to claim 1, wherein:

the distribution image generating includes generating distribution images of the motion velocities by a pattern matching technique between two ultrasonic images in different time phases; and the estimating include an estimation of corresponding points corresponding in each of the remaining time phases on the basis of the distribution images and an interval between the plurality of time phases.

26. An ultrasonic diagnostic apparatus comprising:

a memory which stores a plurality of ultrasonic images which corresponds to a plurality of time phases and are concerning with an object;

a center point of contraction setting unit configured to set a first center point of contraction in a tissue range of the object and a second center point of contraction adjacent to the first center point of contraction;

a distribution image generation unit configured to generate a first distribution images of motion velocities in a direction toward the first center point of contraction and a second distribution images of motion velocities in a direction toward the second center point of contraction on the basis of the plurality of the ultrasonic images;

a tracking point setting unit configured to set tracking points in a tissue range of the object in an image which is one of the plurality of ultrasonic images and corresponds to a predetermined time phase;

an estimation unit configured to estimate first corresponding points which correspond to the tracking points on the basis of the first distribution images of motion velocities and second corresponding points which correspond to the tracking points on the basis of the second distribution images of motion velocities, in the plurality of ultrasound images corresponding to remaining time phases other than the predetermined time phase;

a signal value determining unit configured to determine signal values at the tracking points associated with a stretch of the tissue range in each of the time phases and signal values at the first corresponding points and the second corresponding points in the remaining time phases other than the predetermined time phase;

a motion information image generating unit configured to generate a first motion information image on the basis of the signal values at the tracking points and the first corresponding points and a second motion information image on the basis of the signal values at the tracking points and the second corresponding points;

a compound image generating unit configured to generate a compound image compounded the first motion information image and the second motion information image; and a display unit configured to display the compound image.

27. A motion information image generating method comprising:

generating a plurality of distribution images of motion velocities in a plurality of time phases on the basis of a plurality of a ultrasonic images which corresponds to a plurality of time phases and are concerning with an object;

setting tracking points in a tissue range of the object in an image which is one of the plurality of ultrasonic images and corresponds to a predetermined time phase;

estimating corresponding points which correspond to the tracking points in the plurality of ultrasound images corresponding to remaining time phases other than the predetermined time phase, on the basis of the plurality of distribution images of motion velocities;

determining signal values at the tracking points and the corresponding points in each of the plurality of the time phases according to stretch of the tissue range of the object;

generating a motion information image on the basis of the signal values at the tracking points and the corresponding points; and displaying the motion information image.

28. The motion information image generating method according to claim 27, wherein in the case where a first corresponding point and a second corresponding point in a predetermined time phase overlap at a third corresponding point in a succeeding time phase, the signal value determining includes determination of a signal value of the third corresponding point on the basis of at least a signal value of the first corresponding point and signal value of the second corresponding point.

29. The motion information image generating method according to claim 27, wherein, in the case where a first tracking point and a second tracking point in an initial time phase overlap at a third corresponding point in a succeeding time phase, the signal value determining includes determination a signal value of the third corresponding point on the basis of at least a signal value of the first tracking point and signal value of the second tracking point.

30. The motion information image generating method according to claim 27, wherein the signal value determining includes determination of signal value of a point which is in a tissue range and adjacent to the corresponding points, on the basis of at least a signal value of a nearest corresponding point.

* * * * *